US012758226B2

(12) United States Patent
Milhous et al.

(10) Patent No.: US 12,758,226 B2
(45) Date of Patent: Oct. 13, 2026

(54) FILAMENTARY DEVICES FOR TREATMENT OF VASCULAR DEFECTS

(71) Applicant: MICROVENTION, INC., Aliso Viejo, CA (US)

(72) Inventors: Parker Milhous, Santa Ana, CA (US); Karishma Desai, Mission Viejo, CA (US)

(73) Assignee: MICROVENTION, INC., Aliso Viejo, CA (US)

(*) Notice: Subject to any disclaimer, the term of this patent is extended or adjusted under 35 U.S.C. 154(b) by 516 days.

(21) Appl. No.: 17/572,988

(22) Filed: Jan. 11, 2022

(65) Prior Publication Data

US 2022/0249098 A1 Aug. 11, 2022

Related U.S. Application Data

(63) Continuation of application No. 16/815,911, filed on Mar. 11, 2020, now abandoned.

(Continued)

(51) Int. Cl.
*A61B 17/12* (2006.01)
*A61B 17/00* (2006.01)

(52) U.S. Cl.
CPC .. *A61B 17/12113* (2013.01); *A61B 17/00234* (2013.01); *A61B 17/12145* (2013.01); *A61B 17/12172* (2013.01); *A61B 17/12177* (2013.01); *A61B 2017/00238* (2013.01); *A61B 2017/00867* (2013.01); *A61B 2017/12054* (2013.01)

(58) Field of Classification Search
CPC ........ A61B 17/12172; A61B 17/12177; A61B 17/12168; A61B 17/12118; A61B 17/12113; A61B 17/12109; A61B 17/12122; A61B 17/12145;

(Continued)

(56) References Cited

U.S. PATENT DOCUMENTS

| | | | |
|---|---|---|---|
| 3,874,388 | A | 4/1975 | King et al. |
| 4,282,875 | A | 8/1981 | Serbinenko |

(Continued)

FOREIGN PATENT DOCUMENTS

| | | |
|---|---|---|
| AU | 2009242528 | 3/2016 |
| CA | 2722037 | 10/2009 |

(Continued)

OTHER PUBLICATIONS

A Complete Microcatheter Portfolio; A Broad Selection of Microcatheters. Boston Scientific Brochure 2007.

(Continued)

*Primary Examiner* — Katherine M Shi
*Assistant Examiner* — Mohammed S Adam
(74) *Attorney, Agent, or Firm* — ONE LLP

(57) ABSTRACT

Devices and methods for treatment of a patient's vasculature are described. Embodiments may include a permeable implant having a radially constrained state configured for delivery within a catheter lumen, an expanded state, and a plurality of elongate filaments that are woven together. The permeable implant may include a support structure having a plurality of scaffolding filaments where each of the plurality of scaffolding filaments has a diameter that is larger than a diameter of each of the plurality of elongate filaments of the first permeable shell.

20 Claims, 20 Drawing Sheets

Related U.S. Application Data

(60) Provisional application No. 62/873,256, filed on Jul. 12, 2019.

(58) Field of Classification Search
CPC ........ A61B 17/12031; A61B 17/00234; A61B 2017/00238
See application file for complete search history.

(56) References Cited

U.S. PATENT DOCUMENTS 4,346,712 A 8/1982 Handa et al.
4,402,319 A 9/1983 Handa et al.
4,619,246 A 10/1986 Molgaard-Nielsen et al.
4,675,361 A 6/1987 Ward
4,729,278 A 3/1988 Graeff
4,998,539 A 3/1991 Delsanti
5,061,275 A 10/1991 Wallsten et al.
5,071,407 A 12/1991 Termin et al.
5,108,407 A 4/1992 Geremia et al.
5,122,136 A 6/1992 Guglielmi et al.
5,154,705 A 10/1992 Fleischhacker et al.
5,158,545 A 10/1992 Trudell et al.
5,165,421 A 11/1992 Fleischhacker et al.
5,263,963 A 11/1993 Garrison
5,334,210 A 8/1994 Gianturco
5,378,239 A 1/1995 Termin
5,527,338 A 6/1996 Purdy et al.
5,536,247 A 7/1996 Thornton
5,562,725 A 10/1996 Schmitt et al.
5,569,245 A 10/1996 Guglielmi et al.
5,578,074 A 11/1996 Mirigian
5,591,222 A 1/1997 Susawa et al.
5,601,595 A 2/1997 Smith
5,630,840 A 5/1997 Mayer
D380,266 S 6/1997 Boatman et al.
5,645,559 A 7/1997 Hachtman et al.
5,725,552 A 3/1998 Kotula
5,725,570 A 3/1998 Heath
5,733,294 A 3/1998 Forber
5,749,883 A 5/1998 Halpern
5,759,161 A 6/1998 Ogawa
5,766,219 A 6/1998 Horton
5,846,261 A 12/1998 Kotula et al.
5,873,907 A 2/1999 Frantzen
5,907,893 A 6/1999 Zadno-Azizi
5,916,235 A 6/1999 Guglielmi
5,925,060 A 7/1999 Forber
5,927,345 A 7/1999 Samson
5,928,260 A 7/1999 Chin et al.
5,935,148 A 8/1999 Villar et al.
5,944,733 A 8/1999 Engelson
5,944,738 A 8/1999 Amplatz
5,951,599 A 9/1999 Mccrory
5,964,797 A 10/1999 Ho
5,980,554 A 11/1999 Lenker et al.
5,984,929 A 11/1999 Bashiri et al.
5,989,242 A 11/1999 Saadat et al.
6,033,423 A 3/2000 Ken et al.
6,063,070 A 5/2000 Eder
6,063,104 A 5/2000 Villar et al.
6,086,577 A 7/2000 Ken et al.
6,093,199 A 7/2000 Brown et al.
6,123,715 A 9/2000 Amplatz
6,139,564 A 10/2000 Teoh et al.
6,142,975 A 11/2000 Jalisi et al.
6,152,144 A 11/2000 Lesh et al.
6,156,061 A 12/2000 Wallace et al.
6,159,206 A 12/2000 Ogawa
6,168,615 B1 1/2001 Ken et al.
6,168,618 B1 1/2001 Frantzen
6,168,622 B1 1/2001 Mazzocchi
6,190,402 B1 2/2001 Horton et al.
6,193,708 B1 2/2001 Ken et al.
6,203,779 B1 3/2001 Ricci et al.
6,221,086 B1 4/2001 Forber
6,238,403 B1 5/2001 Greene, Jr. et al.
6,277,126 B1 8/2001 Barry et al.
6,290,721 B1 9/2001 Heath
6,315,709 B1 11/2001 Garibaldi et al.
6,325,815 B1 12/2001 Kusleika
6,342,068 B1 1/2002 Thompson
6,344,048 B1 2/2002 Chin et al.
6,346,117 B1 2/2002 Greenhalgh
6,350,270 B1 2/2002 Roue
6,368,338 B1 4/2002 Konya
6,368,339 B1 4/2002 Amplatz
6,375,668 B1 4/2002 Gifford
6,375,670 B1 4/2002 Greenhalgh
6,383,174 B1 5/2002 Eder
6,391,037 B1 5/2002 Greenhalgh
6,425,914 B1 7/2002 Wallace et al.
6,428,558 B1 8/2002 Jones et al.
6,447,531 B1 9/2002 Amplatz
6,454,780 B1 9/2002 Wallace
6,461,370 B1 10/2002 Gray et al.
6,463,317 B1 10/2002 Kucharczyk
6,468,266 B1 10/2002 Bashiri et al.
6,478,773 B1 11/2002 Gandhi et al.
6,500,149 B2 12/2002 Gandhi et al.
6,506,204 B2 1/2003 Mazzocchi
6,511,468 B1 1/2003 Cragg et al.
6,551,303 B1 4/2003 Van Tassel et al.
6,579,303 B2 6/2003 Amplatz
6,585,748 B1 7/2003 Jeffree
6,589,256 B2 7/2003 Forber
6,589,265 B1 7/2003 Palmer et al.
6,599,308 B2 7/2003 Amplatz
6,605,102 B1 8/2003 Mazzocchi et al.
6,605,111 B2 8/2003 Bose et al.
6,607,539 B1 8/2003 Hayashi et al.
6,613,074 B1 9/2003 Mitelberg
6,626,939 B1 9/2003 Burnside et al.
6,632,241 B1 10/2003 Hancock
6,635,068 B1 10/2003 Dubrul et al.
6,638,257 B2 10/2003 Amplatz
6,652,556 B1 11/2003 Tassel et al.
6,666,882 B1 12/2003 Bose et al.
6,669,721 B1 12/2003 Bose et al.
6,682,546 B2 1/2004 Amplatz
6,689,150 B1 2/2004 Tassel
6,689,486 B2 2/2004 Ho et al.
6,719,778 B1 4/2004 Van Tassel et al.
6,730,119 B1 5/2004 Smalling
6,743,236 B2 6/2004 Barry et al.
6,743,251 B1 6/2004 Eder
6,746,468 B1 6/2004 Sepetka et al.
6,746,890 B2 6/2004 Gupta et al.
6,752,826 B2 6/2004 Holloway et al.
6,780,196 B2 8/2004 Chin et al.
6,811,560 B2 11/2004 Jones et al.
6,818,006 B2 11/2004 Douk et al.
6,855,153 B2 2/2005 Saadat
6,855,154 B2 2/2005 Abdel-Gawwad
6,878,384 B2 4/2005 Cruise et al.
6,936,055 B1 8/2005 Ken et al.
6,940,209 B2 9/2005 Henderson
6,953,472 B2 10/2005 Palmer et al.
6,953,473 B2 10/2005 Porter
6,966,892 B2 11/2005 Gandhi et al.
6,994,092 B2 2/2006 van der Burg et al.
7,001,409 B2 2/2006 Amplatz
7,004,962 B2 2/2006 Stinson
7,011,671 B2 3/2006 Welch
7,044,958 B2 5/2006 Douk et al.
7,052,513 B2 5/2006 Thompson
7,083,632 B2 8/2006 Avellanet et al.
7,101,390 B2 9/2006 Nelson
7,122,043 B2 10/2006 Greenhalgh et al.
7,128,736 B1 10/2006 Abrams et al.
7,179,276 B2 2/2007 Barry et al.
7,182,774 B2 2/2007 Barry et al.
7,195,636 B2 3/2007 Avellanet et al.
7,198,613 B2 4/2007 Gandhi et al.
7,201,918 B2 4/2007 Cruise

(56) References Cited

U.S. PATENT DOCUMENTS

| | | | |
|---|---|---|---|
| 7,229,454 | B2 | 6/2007 | Tran |
| 7,229,461 | B2 | 6/2007 | Chin et al. |
| 7,275,471 | B2 | 10/2007 | Nishri et al. |
| 7,326,225 | B2 | 2/2008 | Ferrera et al. |
| 7,329,279 | B2 | 2/2008 | Haug et al. |
| 7,331,980 | B2 | 2/2008 | Dubrul |
| 7,410,482 | B2 | 8/2008 | Murphy |
| 7,419,503 | B2 | 9/2008 | Pulnev et al. |
| 7,490,396 | B2 | 2/2009 | Bradley |
| 7,524,319 | B2 | 4/2009 | Dubrul |
| 7,569,066 | B2 | 8/2009 | Gerberding |
| 7,573,382 | B2 | 8/2009 | Choubey et al. |
| 7,575,582 | B2 | 8/2009 | Gandhi et al. |
| 7,578,826 | B2 | 8/2009 | Gandhi et al. |
| 7,597,704 | B2 | 10/2009 | Frazier et al. |
| 7,648,532 | B2 | 1/2010 | Greenhalgh et al. |
| 7,695,488 | B2 | 4/2010 | Berenstein |
| 7,722,637 | B2 | 5/2010 | Barry et al. |
| 7,745,732 | B2 | 6/2010 | Michael et al. |
| 7,806,919 | B2 | 10/2010 | Bloom et al. |
| 7,862,577 | B2 | 1/2011 | Gray et al. |
| 7,942,925 | B2 | 5/2011 | Yodaf |
| 7,989,703 | B2 | 8/2011 | Schaffer |
| 8,043,326 | B2 | 10/2011 | Hancock |
| 8,043,329 | B2 | 10/2011 | Khairkhahan |
| 8,066,757 | B2 | 11/2011 | Ferrera et al. |
| 8,142,456 | B2 | 3/2012 | Rosqueta et al. |
| 8,182,506 | B2 | 5/2012 | Fitz et al. |
| 8,192,480 | B2 | 6/2012 | Tieu et al. |
| 8,261,648 | B1 | 9/2012 | Marchand et al. |
| 8,313,505 | B2 | 11/2012 | Amplatz et al. |
| 8,398,670 | B2 | 3/2013 | Amplatz |
| 8,430,012 | B1 | 4/2013 | Marchand |
| 8,506,619 | B2 | 8/2013 | Ortiz et al. |
| 8,551,132 | B2 | 10/2013 | Eskridge et al. |
| 8,597,320 | B2 | 12/2013 | Sepetka |
| 8,597,323 | B1 | 12/2013 | Plaza et al. |
| 8,690,907 | B1 | 4/2014 | Janardhan et al. |
| 8,715,338 | B2 | 5/2014 | Frid |
| 8,728,117 | B1 | 5/2014 | Janardhan et al. |
| 8,747,430 | B2 | 6/2014 | Porter |
| 8,758,395 | B2 | 6/2014 | Kleshinski et al. |
| 8,795,330 | B1 | 8/2014 | Janardhan et al. |
| 8,826,791 | B2 | 9/2014 | Thompson et al. |
| 8,840,735 | B2 | 9/2014 | Schaffer |
| 8,845,679 | B1 | 9/2014 | Janardhan et al. |
| 8,932,317 | B2 | 1/2015 | Marks et al. |
| 9,078,658 | B2 | 7/2015 | Hewitt et al. |
| 9,198,668 | B2 | 12/2015 | Theobald et al. |
| 9,198,670 | B2 | 12/2015 | Hewitt et al. |
| 9,242,070 | B2 | 1/2016 | Tieu |
| 9,259,337 | B2 | 2/2016 | Cox et al. |
| 9,272,323 | B2 | 3/2016 | Schaffer |
| 9,295,473 | B2 | 3/2016 | Hewitt et al. |
| 9,351,715 | B2 | 5/2016 | Mach |
| 9,414,819 | B2 | 8/2016 | Fitz et al. |
| 9,492,174 | B2 | 11/2016 | Hewitt et al. |
| 9,504,588 | B2 | 11/2016 | Sadisivan et al. |
| 9,561,125 | B2 | 2/2017 | Bowman et al. |
| 9,585,669 | B2 | 3/2017 | Becking et al. |
| 9,597,087 | B2 | 3/2017 | Marchand et al. |
| 9,629,635 | B2 | 4/2017 | Hewitt et al. |
| 9,687,245 | B2 | 6/2017 | Molaei et al. |
| 9,717,500 | B2 | 8/2017 | Tieu et al. |
| 9,855,047 | B2 | 1/2018 | Berez et al. |
| 9,867,622 | B2 | 1/2018 | Bowman |
| 9,949,739 | B2 | 4/2018 | Tsukashima et al. |
| 9,955,976 | B2 | 5/2018 | Hewitt et al. |
| 9,968,358 | B2 | 5/2018 | Tieu et al. |
| 10,076,338 | B2 | 9/2018 | Fitz et al. |
| 10,123,803 | B2 | 11/2018 | Ferrera et al. |
| 10,130,372 | B2 | 11/2018 | Griffin |
| 10,136,896 | B2 | 11/2018 | Hewitt et al. |
| 10,238,393 | B2 | 3/2019 | Marchand et al. |
| 10,260,182 | B2 | 4/2019 | Thompson et al. |
| 10,260,183 | B2 | 4/2019 | Marchand et al. |
| 10,398,441 | B2 | 9/2019 | Warner et al. |
| 10,426,589 | B2 | 10/2019 | Van der Burg et al. |
| 10,470,773 | B2 | 11/2019 | Maguire et al. |
| 10,617,426 | B2 | 4/2020 | Aboytes et al. |
| 10,716,573 | B2 | 7/2020 | Connor |
| 10,736,758 | B2 | 8/2020 | Ruvalcaba et al. |
| 10,813,645 | B2 | 10/2020 | Hewitt et al. |
| 10,856,880 | B1 | 12/2020 | Badruddin et al. |
| 10,939,914 | B2 | 3/2021 | Hewitt et al. |
| 10,952,739 | B2 | 3/2021 | Plaza et al. |
| 11,033,277 | B2 | 6/2021 | Wolfe et al. |
| 11,058,431 | B2 | 7/2021 | Pereira et al. |
| 11,185,335 | B2 | 11/2021 | Badruddin et al. |
| 11,202,636 | B2 | 12/2021 | Zaidat et al. |
| 11,284,901 | B2 | 3/2022 | Griffin |
| 11,317,921 | B2 | 5/2022 | Hewitt et al. |
| 11,389,174 | B2 | 7/2022 | Griffin |
| 11,464,518 | B2 | 10/2022 | Connor |
| 11,559,309 | B2 | 1/2023 | Rangwala et al. |
| 11,723,667 | B2 | 8/2023 | Hewitt et al. |
| 11,786,253 | B2 | 10/2023 | Divino et al. |
| 2001/0031981 | A1 | 10/2001 | Evans et al. |
| 2002/0065552 | A1 | 5/2002 | Jayaraman et al. |
| 2002/0103542 | A1 | 8/2002 | Bilbo |
| 2002/0111647 | A1 | 8/2002 | Khairkhahan et al. |
| 2002/0143349 | A1 | 10/2002 | Gifford, III et al. |
| 2002/0143361 | A1 | 10/2002 | Douk et al. |
| 2002/0156499 | A1 | 10/2002 | Konya et al. |
| 2002/0169473 | A1 | 11/2002 | Sepetka et al. |
| 2002/0183787 | A1 | 12/2002 | Wahr et al. |
| 2002/0187288 | A1 | 12/2002 | Lim et al. |
| 2003/0012816 | A1 | 1/2003 | West et al. |
| 2003/0028209 | A1 | 2/2003 | Teoh et al. |
| 2003/0040771 | A1 | 2/2003 | Hyodoh et al. |
| 2003/0167068 | A1 | 9/2003 | Amplatz |
| 2003/0171739 | A1 | 9/2003 | Murphy et al. |
| 2003/0171774 | A1 | 9/2003 | Freudenthal et al. |
| 2003/0181942 | A1 | 9/2003 | Sutton et al. |
| 2003/0187473 | A1 | 10/2003 | Berenstein et al. |
| 2003/0199913 | A1 | 10/2003 | Dubrul et al. |
| 2004/0059370 | A1 | 3/2004 | Green, Jr. et al. |
| 2004/0098027 | A1 | 5/2004 | Tech et al. |
| 2004/0111147 | A1 | 6/2004 | Rabkin et al. |
| 2004/0122367 | A1 | 6/2004 | Sculati et al. |
| 2004/0143239 | A1 | 7/2004 | Zhou et al. |
| 2004/0158311 | A1 | 8/2004 | Berhow |
| 2004/0172053 | A1 | 9/2004 | Barry et al. |
| 2004/0186562 | A1 | 9/2004 | Cox |
| 2004/0193206 | A1 | 9/2004 | Gerberding et al. |
| 2004/0193208 | A1 | 9/2004 | Talpade et al. |
| 2004/0220563 | A1 | 11/2004 | Eder |
| 2004/0260333 | A1 | 12/2004 | Dubrul et al. |
| 2005/0021075 | A1 | 1/2005 | Bonnette et al. |
| 2005/0033408 | A1 | 2/2005 | Jones et al. |
| 2005/0053782 | A1 | 3/2005 | Sen et al. |
| 2005/0096728 | A1 | 5/2005 | Ramer |
| 2005/0112349 | A1 | 5/2005 | Laurencin et al. |
| 2005/0113861 | A1 | 5/2005 | Corcoran et al. |
| 2005/0113868 | A1 | 5/2005 | Devellian et al. |
| 2005/0119684 | A1 | 6/2005 | Gutterman et al. |
| 2005/0133046 | A1 | 6/2005 | Becker et al. |
| 2005/0137623 | A1 | 6/2005 | Jones et al. |
| 2005/0149173 | A1 | 7/2005 | Hunter et al. |
| 2005/0216052 | A1 | 9/2005 | Mazzocchi et al. |
| 2005/0222489 | A1 | 10/2005 | Rahdert et al. |
| 2005/0228422 | A1 | 10/2005 | Machold et al. |
| 2005/0228434 | A1 | 10/2005 | Amplatz et al. |
| 2005/0267516 | A1 | 12/2005 | Soleimani et al. |
| 2005/0277978 | A1 | 12/2005 | Greenhalgh |
| 2006/0009798 | A1 | 1/2006 | Callister et al. |
| 2006/0009799 | A1 | 1/2006 | Kleshinski et al. |
| 2006/0009800 | A1 | 1/2006 | Christianson et al. |
| 2006/0052815 | A1 | 3/2006 | Fitz et al. |
| 2006/0052816 | A1 | 3/2006 | Bates et al. |
| 2006/0064151 | A1 | 3/2006 | Guterman et al. |
| 2006/0083721 | A1 | 4/2006 | Cohen et al. |
| 2006/0106421 | A1 | 5/2006 | Teoh |
| 2006/0116708 | A1 | 6/2006 | Ogawa et al. |

(56) References Cited

U.S. PATENT DOCUMENTS

2006/0135947 A1 6/2006 Soltesz et al.
2006/0155323 A1 7/2006 Porter et al.
2006/0178694 A1 8/2006 Greenhalgh et al.
2006/0200192 A1 9/2006 Fitz et al.
2006/0200234 A1 9/2006 Hines
2006/0206140 A1 9/2006 Shaolian et al.
2006/0212055 A1 9/2006 Karabey et al.
2006/0217799 A1 9/2006 Mailander et al.
2006/0235464 A1 10/2006 Avellanet et al.
2006/0247680 A1 11/2006 Amplatz et al.
2006/0252984 A1 11/2006 Rahdert et al.
2006/0253149 A1 11/2006 Gandhi et al.
2006/0271086 A1 11/2006 Ramzipoor et al.
2007/0021816 A1 1/2007 Rudin
2007/0031584 A1 2/2007 Roth
2007/0061006 A1 3/2007 Desatnik et al.
2007/0088387 A1 4/2007 Eskridge et al.
2007/0100419 A1 5/2007 Licata et al.
2007/0106311 A1 5/2007 Wallace et al.
2007/0106323 A1 5/2007 Barry et al.
2007/0112380 A1 5/2007 Figulla et al.
2007/0142906 A1 6/2007 Figulla et al.
2007/0144124 A1 6/2007 Schewe et al.
2007/0167911 A1 7/2007 Gandhi et al.
2007/0167980 A1 7/2007 Figulla et al.
2007/0173928 A1 7/2007 Morsi
2007/0203062 A1 8/2007 Ellis-Behnke et al.
2007/0208373 A1 9/2007 Zaver et al.
2007/0208376 A1 9/2007 Meng
2007/0225760 A1 9/2007 Moszner et al.
2007/0233186 A1 10/2007 Meng
2007/0255388 A1 11/2007 Rudakov et al.
2007/0265656 A1 11/2007 Amplatz et al.
2007/0288083 A1 12/2007 Hines
2007/0299464 A1 12/2007 Cruise et al.
2008/0033341 A1 2/2008 Grad
2008/0033366 A1 2/2008 Matson
2008/0033475 A1 2/2008 Meng
2008/0033478 A1 2/2008 Meng
2008/0097495 A1 4/2008 Feller, III et al.
2008/0119886 A1 5/2008 Greenhalgh et al.
2008/0161936 A1 7/2008 Feller et al.
2008/0188923 A1 8/2008 Chu
2008/0195139 A1 8/2008 Donald et al.
2008/0200945 A1 8/2008 Amplatz et al.
2008/0221600 A1 9/2008 Dieck et al.
2008/0228215 A1 9/2008 Strauss et al.
2008/0262518 A1 10/2008 Freudenthal
2008/0281350 A1 11/2008 Sepetka et al.
2009/0025820 A1 1/2009 Adams
2009/0062812 A1 3/2009 Fitz et al.
2009/0062834 A1 3/2009 Moftakhar
2009/0062841 A1 3/2009 Amplatz et al.
2009/0082803 A1 3/2009 Adams et al.
2009/0099647 A1 4/2009 Glimsdale et al.
2009/0112305 A1 4/2009 Goldmann et al.
2009/0132024 A1 5/2009 Berkhoff
2009/0163780 A1 6/2009 Tieu
2009/0227976 A1 9/2009 Calabria
2009/0275974 A1 11/2009 Marchand
2009/0287291 A1 11/2009 Becking et al.
2009/0287294 A1 11/2009 Rosqueta et al.
2009/0318948 A1 12/2009 Linder et al.
2010/0004679 A1 1/2010 Osypka
2010/0023048 A1 1/2010 Mach
2010/0023105 A1 1/2010 Levy et al.
2010/0036473 A1 2/2010 Roth
2010/0069948 A1 3/2010 Veznedaroglu et al.
2010/0094409 A1 4/2010 Barker et al.
2010/0106235 A1 4/2010 Kariniemi et al.
2010/0262182 A1 10/2010 Moszner et al.
2011/0022149 A1 1/2011 Cox
2011/0029008 A1 2/2011 Gesswein
2011/0046658 A1 2/2011 Connor et al.
2011/0046719 A1 2/2011 Frid
2011/0054515 A1 3/2011 Bridgeman
2011/0082493 A1 4/2011 Samson et al.
2011/0144669 A1 6/2011 Becking et al.
2011/0152823 A1 6/2011 Mohiuddin et al.
2011/0152993 A1* 6/2011 Marchand ........ A61B 17/12113 623/1.2
2011/0202085 A1 8/2011 Loganathan et al.
2011/0208227 A1 8/2011 Becking
2011/0208233 A1 8/2011 McGuckin
2011/0224776 A1 9/2011 Sepekta et al.
2011/0295298 A1 12/2011 Moszner
2011/0319926 A1 12/2011 Becking
2012/0065667 A1 3/2012 Javois et al.
2012/0143237 A1 6/2012 Cam
2012/0165919 A1 6/2012 Cox et al.
2012/0197283 A1 8/2012 Marchand et al.
2012/0271337 A1 10/2012 Figulla et al.
2012/0283768 A1 11/2012 Cox et al.
2012/0330341 A1 12/2012 Becking et al.
2013/0066357 A1 3/2013 Aboytes et al.
2013/0092012 A1 4/2013 Marchand et al.
2013/0092013 A1 4/2013 Thompson et al.
2013/0116722 A1 5/2013 Aboytes et al.
2013/0123830 A1 5/2013 Becking et al.
2013/0211495 A1 8/2013 Halden et al.
2013/0233160 A1 9/2013 Marchand et al.
2013/0239790 A1 9/2013 Thompson et al.
2013/0245667 A1 9/2013 Marchand et al.
2013/0268053 A1 10/2013 Molaei et al.
2013/0274862 A1 10/2013 Cox et al.
2013/0274863 A1 10/2013 Cox et al.
2013/0274866 A1 10/2013 Cox et al.
2013/0274868 A1 10/2013 Cox et al.
2013/0296912 A1 11/2013 Ottma
2013/0325051 A1 12/2013 Martin et al.
2014/0005713 A1 1/2014 Bowman et al.
2014/0005714 A1 1/2014 Quick et al.
2014/0018841 A1 1/2014 Peiffer et al.
2014/0052233 A1 2/2014 Cox et al.
2014/0058436 A1 2/2014 Rosenbluth et al.
2014/0074151 A1 3/2014 Tischler et al.
2014/0135734 A1 5/2014 Dakin et al.
2014/0135817 A1 5/2014 Tischler et al.
2014/0135827 A1 5/2014 Amplatz et al.
2014/0142611 A1 5/2014 Plaza et al.
2014/0172001 A1 6/2014 Becking et al.
2014/0200607 A1 7/2014 Sepetka et al.
2014/0257360 A1 9/2014 Keillor
2014/0257361 A1 9/2014 Prom
2014/0318354 A1 10/2014 Thompson et al.
2014/0318355 A1 10/2014 Marchand et al.
2014/0330299 A1 11/2014 Rosenbluth et al.
2014/0358178 A1 12/2014 Hewitt et al.
2015/0012033 A1 1/2015 Plaza et al.
2015/0133989 A1 5/2015 Lubock et al.
2015/0182674 A1 7/2015 Schaffer
2015/0272589 A1 10/2015 Lorenzo
2015/0283363 A1 10/2015 Hewitt et al.
2015/0297238 A1 10/2015 Ken
2015/0313605 A1 11/2015 Griffin
2015/0374483 A1 12/2015 Janardhan et al.
2016/0015396 A1 1/2016 Cox et al.
2016/0015398 A1 1/2016 Hewitt et al.
2016/0030052 A1 2/2016 Cragg et al.
2016/0045201 A1 2/2016 Rosenbluth et al.
2016/0100842 A1 4/2016 Plaza et al.
2016/0192941 A1 7/2016 Hewitt et al.
2016/0249934 A1 9/2016 Hewitt et al.
2016/0249935 A1 9/2016 Hewitt et al.
2016/0249937 A1 9/2016 Marchand et al.
2016/0262769 A1 9/2016 Cragg et al.
2016/0324528 A1 11/2016 Hebert et al.
2016/0324668 A1 11/2016 Wallace et al.
2016/0335757 A1 11/2016 Florent et al.
2016/0367260 A9 12/2016 Hewitt et al.
2017/0035437 A1 2/2017 Sarge et al.
2017/0079662 A1 3/2017 Rhee et al.
2017/0088988 A1 3/2017 Thompson et al.
2017/0095254 A1 4/2017 Hewitt et al.

(56) References Cited

U.S. PATENT DOCUMENTS

| | | | |
|---|---|---|---|
| 2017/0128077 A1 | 5/2017 | Hewitt et al. | |
| 2017/0191195 A1 | 7/2017 | Marchand et al. | |
| 2017/0224350 A1 | 8/2017 | Shimizu et al. | |
| 2017/0245862 A1 | 8/2017 | Cox et al. | |
| 2017/0258473 A1 | 9/2017 | Plaza et al. | |
| 2018/0000489 A1 | 1/2018 | Marchand et al. | |
| 2018/0070955 A1 | 3/2018 | Greene, Jr. et al. | |
| 2018/0140305 A1 | 5/2018 | Connor | |
| 2018/0153554 A1 | 6/2018 | Walzman | |
| 2018/0185130 A1 | 7/2018 | Janardhan et al. | |
| 2018/0206849 A1 | 7/2018 | Hewitt et al. | |
| 2018/0206851 A1 | 7/2018 | Walzman | |
| 2018/0271540 A1 | 9/2018 | Merritt et al. | |
| 2018/0303486 A1 | 10/2018 | Rosenbluth et al. | |
| 2018/0333588 A1 | 11/2018 | Lieber et al. | |
| 2018/0338767 A1 | 11/2018 | Dasnurkar et al. | |
| 2019/0046209 A1 | 2/2019 | Plaza et al. | |
| 2019/0059909 A1 | 2/2019 | Griffin | |
| 2019/0192166 A1 | 6/2019 | Hewitt et al. | |
| 2019/0192167 A1 | 6/2019 | Lorenzo | |
| 2019/0209180 A1 | 7/2019 | Kealey et al. | |
| 2019/0218696 A1 | 7/2019 | Thompson et al. | |
| 2019/0223876 A1 | 7/2019 | Badruddin et al. | |
| 2019/0223878 A1 | 7/2019 | Lorenzo et al. | |
| 2019/0223881 A1 | 7/2019 | Hewitt et al. | |
| 2019/0269414 A1 | 9/2019 | Griffin | |
| 2019/0290286 A1* | 9/2019 | Divino | A61B 17/12186 |
| 2019/0298364 A1 | 10/2019 | Walsh et al. | |
| 2019/0343533 A1 | 11/2019 | Costalat | |
| 2019/0365385 A1 | 12/2019 | Gorochow et al. | |
| 2020/0038035 A1 | 2/2020 | Griffin | |
| 2020/0113576 A1 | 4/2020 | Gorochow et al. | |
| 2020/0289124 A1 | 9/2020 | Rangwala et al. | |
| 2020/0289125 A1 | 9/2020 | Dholakia et al. | |
| 2020/0289126 A1 | 9/2020 | Hewitt et al. | |
| 2020/0337710 A1 | 10/2020 | Lorenzo et al. | |
| 2020/0367894 A1 | 11/2020 | Pereira et al. | |
| 2020/0367896 A1 | 11/2020 | Zaidat et al. | |
| 2020/0367898 A1* | 11/2020 | Gorochow | A61B 17/12172 |
| 2021/0007754 A1 | 1/2021 | Milhous et al. | |
| 2021/0007755 A1 | 1/2021 | Lorenzo et al. | |
| 2021/0128161 A1 | 5/2021 | Nageswaran et al. | |
| 2021/0128165 A1 | 5/2021 | Pulugurtha et al. | |
| 2021/0153871 A1 | 5/2021 | Griffin | |
| 2021/0177429 A1 | 6/2021 | Lorenzo | |
| 2021/0212698 A1 | 7/2021 | Connor | |
| 2021/0236279 A1 | 8/2021 | Yohanan et al. | |
| 2021/0275184 A1 | 9/2021 | Hewitt et al. | |
| 2022/0192678 A1 | 6/2022 | Hewitt et al. | |
| 2022/0257260 A1 | 8/2022 | Hewitt et al. | |
| 2022/0323084 A1 | 10/2022 | Griffin | |

FOREIGN PATENT DOCUMENTS

| | | |
|---|---|---|
| CN | 106974691 | 7/2017 |
| EP | 0706876 | 7/2000 |
| EP | 0808138 | 5/2005 |
| EP | 1576929 | 9/2005 |
| EP | 1844717 | 10/2007 |
| EP | 1923019 | 5/2008 |
| EP | 2055263 | 6/2009 |
| EP | 2258275 | 12/2011 |
| EP | 2596754 | 5/2013 |
| EP | 2157937 | 3/2017 |
| FR | 2333169 | 6/1997 |
| JP | 52141092 | 11/1977 |
| JP | H4-47415 | 4/1992 |
| WO | WO 95/30384 | 11/1995 |
| WO | WO 96/01591 | 1/1996 |
| WO | WO 97/26939 | 7/1997 |
| WO | WO 99/03404 | 1/1999 |
| WO | WO 99/05977 | 2/1999 |
| WO | WO 99/62432 | 12/1999 |
| WO | WO 01/45571 | 6/2001 |
| WO | WO 01/93782 | 12/2001 |
| WO | WO 02/00139 | 1/2002 |
| WO | WO 03/011151 | 2/2003 |
| WO | WO 03/032818 | 4/2003 |
| WO | WO 03/063732 | 8/2003 |
| WO | WO 2004/047649 | 6/2004 |
| WO | WO 2004/093742 | 11/2004 |
| WO | WO 2005/117718 | 12/2005 |
| WO | WO 2006/026744 | 3/2006 |
| WO | WO 2006/055683 | 5/2006 |
| WO | WO 2007/006139 | 1/2007 |
| WO | WO 2007/096183 | 8/2007 |
| WO | WO 2008/151204 | 12/2008 |
| WO | WO 2009/036219 | 3/2009 |
| WO | WO 2009/048700 | 4/2009 |
| WO | WO 2009/121006 | 10/2009 |
| WO | WO 2009/126747 | 10/2009 |
| WO | WO 2009/132045 | 10/2009 |
| WO | WO 2009/134337 | 11/2009 |
| WO | WO 2009/135166 | 11/2009 |
| WO | WO 2010/134914 | 11/2010 |
| WO | WO 2011/057002 | 5/2011 |
| WO | WO 2013/102848 | 7/2013 |
| WO | WO 2013/119332 | 8/2013 |
| WO | WO 2014/087245 | 6/2014 |
| WO | WO 2014/169261 | 10/2014 |
| WO | WO 2015/160721 | 10/2015 |
| WO | WO 2015/171268 | 11/2015 |
| WO | WO 2015/192019 | 12/2015 |
| WO | WO 2017/153603 | 9/2017 |
| WO | WO 2018/051187 | 3/2018 |
| WO | WO 2018/058033 | 3/2018 |
| WO | WO 2019/040494 | 2/2019 |
| WO | WO 2021/183793 A2 | 9/2021 |
| WO | WO 2022/198240 | 9/2022 |
| WO | WO 2023/283598 | 1/2023 |

OTHER PUBLICATIONS

Allen et al., "Micromachine Wedge Stepping Motor," pp. 1-6, Nov. 12-20, 1998 ASME International Mechanical Engineering Congress, Anaheim, CA.

Altes et al., "Creation of Saccular Aneurysms in the Rabbit: A model Suitable for Testing Endovascular Devices," American Roentgen Ray Society, Feb. 2000.

Ansari et al., "Thrombosis of a Fusiform Intracranial Aneurysm Induced by Overlapping Neuroform Stents: Case Report," *Neurosurgery*, E950-E951 vol. 60, No. 5, May 2007.

Atritech Press Release, Minneapolis, Jun. 18, 2007 "Atritech Announces Intellectual Property Acquisition, Transaction Establishes Company as leader in Left Atrial Appendage Market."

Caroff, J. et al., "Woven Endobridge (WEB) Device for endovascular treatment of ruptured intracranial wide-neck aneurysms: a single-center experience," *Neuroradiology*, 56(9):755-761 (Sep. 2014).

Caroff, J. et al., "Role of C—Arm VasoCT in the Use of Endovascular WEB Flow Disruption in Intracranial Aneurysm Treatment," *AJNR Am. J. Neuroradiol.* 35(7):1353-1357 (Jul. 2014).

Colla, R. et al., "Treatment of Wide-Neck Basilar Tip Aneurysms Using the Web II Device," *The Neuroradiology Journal* 26(6):669-677 (Dec. 2013).

De Backer, O. et al., "Percutaneous left atrial appendage occlusion for stroke prevention in atrial fibrillation: an update," *Open Heart*, 4:1-14 (2013).

Ding, Y.H. et al., "The Woven EndoBridge: A New Aneurysm Occlusion Device," *AJNR Am. J. Neruradiol.* 32:607-611 (Mar. 2011).

Duerig, T.W., "The Use of Superelasticity in Modern Medicine," MRS Bulletin, pp. 101-104 (Feb. 2002).

Fiorella, D. et al., "Interobserver variability in the assessment of aneurysm occlusion with the WEB aneurysm embolization system," *J. NeuroIntervent. Surg.* Jul. 1, 2014, pii: neurintsurg-2014-011251. doi: 10.1136/neurintsurg-2014-011251 [Epub ahead of print].

Fort Wayne Metals HHS Tube brochure, p. 28-29 (2009), Fort Wayne, Indiana, www.oldsite.fwmetals.com.

Grabenwoger et al., "Endothelialization of Biosynthetic vascular Prosthesis After Laser Perforation," *Ann Thorac Surg*, 66:S110-S114 (1998).

(56) References Cited

OTHER PUBLICATIONS

Guider Softip XF Guide Catheters Brochure, Boston Scientific Corporation 2004.
Gupta et al., "Nitinol Thin Film Three Dimensional Devices-Fabrication and Applications," From: SMST-2003: Proceedings of the International Conference on Shape Memory and Superelastic Technologies Published: 2004.
Hill et al., "Initial Results of the AMPLATZER® Vascular Plug in the treatment of Congenital Heart Disease," Technology and Services, *Business Briefing: US Cardiology*, pp. 1-3 (2004).
Jeffree et al., "The Porus, Guidewire-Directed, Detachable Aneurysm Liner: A New Concept in the Endovascular Treatment of Intracranial Aneurysms," *AJNR Am J Neuradiol* 20:774-779 (May 1999).
Kallmes et al., "A New Endoluminal, Flow-Disrupting Device for Treatment of Saccular Eneurysms," *Stroke*, Journal of the American Heart Association 38:1-7 (2007).
Klisch, J. et al., "The Woven EndoBridge Cerebral Aneurysm Embolization Device (WEB II): initial clinical experience," *Neuroradiology* 53:599-607 (2011).
Konya, A. et al., "Preliminary Results with a New Vascular Basket Occluder in Swine," *JVIR*, 10(8): 1043-1049 (1999).
Kwon et al., "Preliminary Results of the Luna Aneurysm Embolization System in a Rabbit Model: A New Intrasaccular Aneurysm Occlusion Device," *AJNR Am J Neuroradiol*, 32:602-606 (Mar. 2011).
Lendlein, A. et al., "Shape-Memory Polymers," *Angew. Chem. Int. Ed*., 41:2034-2057 (2002).
Lendlein, A. et al., "Biodegradable, Elastic Shape-Memory Polymers for Potential Biomedical Applications," *Science* 296:1673-1676 (May 31, 2002).
Lieber, B.B. et al., "The Role of Blood Impulse in Cerebral Aneurysm Coil Compaction: Effect of Aneurysm Neck Size," IMECE2003-43099, Proceedings of IMECE '03, 2003 ASME International Mechanical Engineering Congress, Washington, D.C. (Nov. 15-21, 2003).
Liu, C. et al., "Review of progress in shape-memory polymers," *J. Mater. Chem*. 17:1543-1558 (2007).
Lubicz, B. et al., "WEB Device for Endovascular Treatment of Wide-Neck Bifurcation Aneurysms," *AJNR Am. J. Neuroradiol*. 34(6):1209-1214 (Jun.-Jul. 2013).
Lubicz, B. et al., "WEB-DL Endovascular Treatment of Wide-Neck Bifurcation Aneurysms: Short- and Midterm Results in a European Study," *AJNR Am. J. Neuroradiol*. 35(3):432-438 (Mar. 2014). doi: 10.3174/ajnr.A3869. Epub Jan. 23, 2014.
Major, S. et al., "Life of Nitinol Drawn Filed Wires with Ag or Au Core for Medical Application," *International Journal of Mechanics* 2(7):73-80 (2013).
Matinlinna et al., "An Introduction to Silanes and Their Clinical Applications in Dentistry," *The International Journal of Prosthodontics*, 17(2):155-164 (2004).
Mine et al., "Intrasaccular flow-diversion for treatment of intracranial aneurysms: the Woven EndoBridge," *Expert Rev. Med. Devices*11(3): 315-325 (May 2014). doi: 10.1586/17434440.2014.907741. Epub Apr. 2, 2014.
Nakayama et al., "Development of Microporous Covered Stents: Geometrical Design of the Luminal Surface," *The International Journal of Artificial Organs*, 28(6):600-608 (2005).
Nemat-Nasser, S. et al., "Superelastic and cyclic response of NiTi SMA at various strain rates and temperatures," *Mechanics of Materials* 38:463-474 (2006).
Nishi et al., "Embolization of experimental aneurysms using a heparin-loaded stent graft with micropores," *Cardiovascular Radiation Medicine* 4:29-33 (2003).
Nishi et al., "Occlusion of Experimental Aneurysms with Heparin-Loaded, Microporous Stent Grafts," *Neurosurgery* 53(6):1397-1405 (Dec. 2003).
Papagiannaki, C. et al., "WEB Intrasaccular Flow Disruptor—Prospective, Multicenter Experience in 83 Patients with 85 Aneurysms," *AJNR Am. J. Neuroradiol*. 35(11):2106-2111 (Nov.-Dec. 2014). 35(11):2106-11. doi: 10.3174/ajnr.A4028. Epub Jul. 3, 2014.
Park, J. et al., "Percutaneous Left Atrial Appendage Transcatheter Occlusion (PLAATO) for Stroke Prevention in Atrial Fibrillation: 2-Year Outcome," *J Invasive. Cardiol*., 21(9):446-450 (2009).
Pelton, A.R. et al., "Optimisation of processing and properties of medical grade Nitinol wire," *Min. Invas. Ther. & Allied Technol*. 9(1):107-118 (2000).
Pham, Q. et al., "Electrospinning of Polymeric Nanofibers for Tissue Engineering Applications: A Review," *Tissue Engr* 12(5):1197-1211 (1996).
Pierot, L. et al., "Intrasaccular Flow-Disruption Treatment of Intracranial Aneurysms: Preliminary Results of a Multicenter Clinical Study," *AJNR Am J Neuroradiol*. 33(7):1232-1238 (Aug. 2012). doi: 10.3174/ajnr.A3191. Epub Jun. 7, 2012.
Pierot, L. et al., "Endovascular WEB Flow Disruption in Middle Cerebral Artery Aneurysms: Preliminary Feasibility, Clinical, and Anatomical Results in a Multicenter Study," *Neurosurgery* 73(1):27-35 (Jul. 2013).
Pierot, L. et al., "Role, safety, and efficacy of WEB flow disruption: a review," *EJMINT Invited Review*, 2014: 1419000139 (May 8, 2014).
Peirot, L. et al., "WEB Treatment of Intracranial Aneurysms: Feasiblity, Complications, and 1-Month Safety Results with the WEB DL and WEB SL/SLS in the French Observatory," *AJNR Am J Neuroradiol*. Feb. 5, 2015 [Epub ehead ofprint].
Romero, J. et al., "Left Atrial Appendage Closure Devices," Clinical Medicine Insights: *Cardiology*, 8:45-52 (2014).
Rottiers, W. et al., "Shape Memory Materials and their applications," in Korolev's readings: conference proceedings, pp. 250-250 (2011).
Salamat et al., "Experimental Evaluation of a New Transcatheter Vascular Embolization Device in the Swine Model," *J Vasc Interv Radiol*, 12:301-311 (2002).
Schaffer, J.E. et al., "Engineering Characteristics of Drawn Filled Nitinol Tube," SMST-2003: Proceedings of the International Conference on Shape Memory and Superelastic Technologies (ASM International), pp. 109-118 (2004).
Schmitz-Rode, T. et al., "Self-expandable spindle for transcatheter vascular occlusion: in vivo experiments. Work in progress." *Radiology* 188:95-100 (Jul. 1993).
Simgen, A. et al., "Evaluation of a newly designed flow diverter for the treatment of intracranial aneurysms in an elastase-induced aneurysm model, in New Zealand white rabbits," *Neuroradiology* 56:129-137 (2014).
Spelle, L. et al., "Letter to the Editor," *Neuroradiol J*. Jun. 2014; 27(3):369. doi: 10.15274/NRJ-2014-10048. Epub Jun. 17, 2014.
Stoeckel, D. et al., "Self-expanding nitinol stents: material and design considerations," *Eur. Radiol*. 14:292-301 (2004).
Turk, A. et al., "Evaluation of the TriSpan Neck Bridge Device for the Treatment of Wide-Necked Aneurysms: An Experimental Study in Canines, Editorial Comment: An Experimental Study in Canines," *Stroke* 32:492-497 (Feb. 2001).
Wallner, A.K. et al., "Coiling after Treatment with the Woven EndoBridge Cerebral Aneurysm Embolization Device," *Interventional Neuroradiology* 18:208-212 (2012).
Yeow, W.L. et al., Device- and LAA-Specific Characteristics for Successful LAA Closures: Tips and Tricks, *Intervent. Cardiol. Clin*., 3:239-254 (2014).
Zimmermann et al., "Patent Foramen Oval Closure With the SeptRx Device, Initial Experience with the First "In-Tunnel" Device," *JACC Cardiovascular Interventions* vol. 3, No. 9., 2010.
International Search Report and Written Opinion mailed Oct. 31, 2008 for International Application No. PCT/US2008/065694.
International Search Report and Written Opinion mailed Nov. 26, 2009 for International Application No. PCT/US2009/042592.
International Search Report and Written Opinion mailed Jul. 28, 2011 for International Application No. PCT/US2010/055494.
International Search Report and Written Opinion mailed Jul. 21, 2015 for International Application No. PCT/US2015/025609.
International Search Report and Written Opinion mailed Jan. 11, 2016 for International Application No. PCT/US2015/025613.

(56) References Cited

OTHER PUBLICATIONS

International Search Report and Written Opinion mailed Jun. 10, 2020 for International Application No. PCT/US2020/022275.
International Search Report and Written Opinion mailed Jun. 11, 2020 for International Application No. PCT/US2020/022364.
International Search Report and Written Opinion mailed Jun. 15, 2020 for International Application No. PCT/US2020/022319.
International Search Report and Written Opinion mailed Jul. 24, 2020 for International Application No. PCT/US2020/022096.
Extended European Search Report dated Apr. 24, 2014, in EP Appl No. EP 08770070 filed Jun. 3, 2008.
Extended European Search Report dated Jul. 30, 2014, in EP Appl No. EP 10829110 filed Nov. 4, 2010.
Extended European Search Report dated Dec. 13, 2017, in EP Appl No. EP 15789225.8 filed Jun. 5, 2015.
Official Action dated Mar. 8, 2019, in JP Appl. No. 2016-562549 filed Jun. 5, 2015.
Spelle, L. et al., "CLinical Assessment of WEB device in Ruptured aneurYSms (CLARYS): 12-month angiographic results of a multi-center study", J NeuroIntervent Surg, 2022, 0:1-6.
International Search Report and Written Opinion mailed Feb. 28, 2023 for International Application No. PCT/US2022/048938.
International Search Report and Written Opinion mailed Jul. 18, 2023, for International Application No. PCT/US2023/20560.
Final Official Action dated Mar. 12, 2024, in JP Appl. No. 2022-169903.
WO, PCT/US2023/036943 ISR and Written Opinion, Mar. 14, 2024.
EP, 22890813.3 Extended Search Report, Aug. 8, 2025.

* cited by examiner

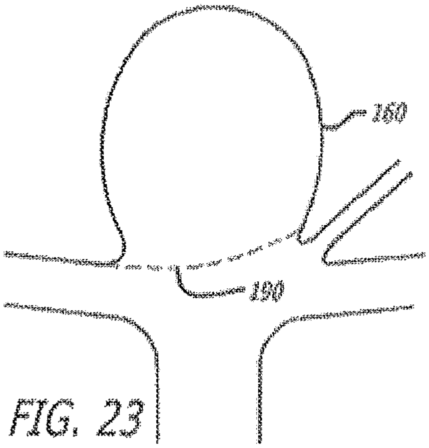
FIG. 23
FIG. 24
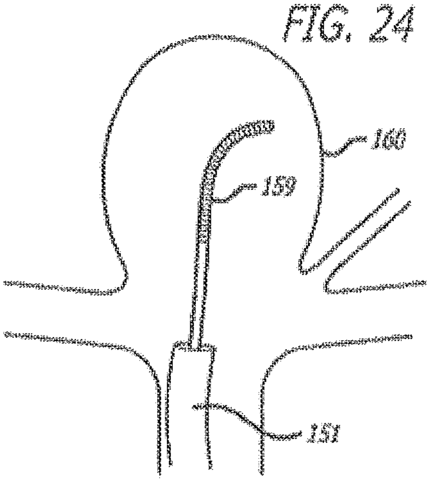
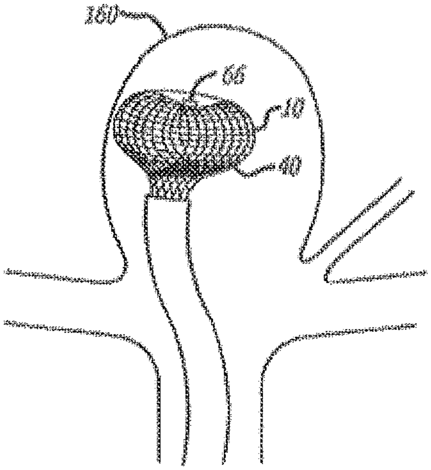
FIG. 25
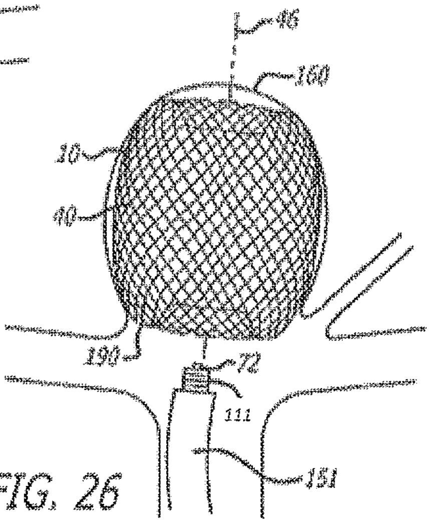
FIG. 26

FIG. 27
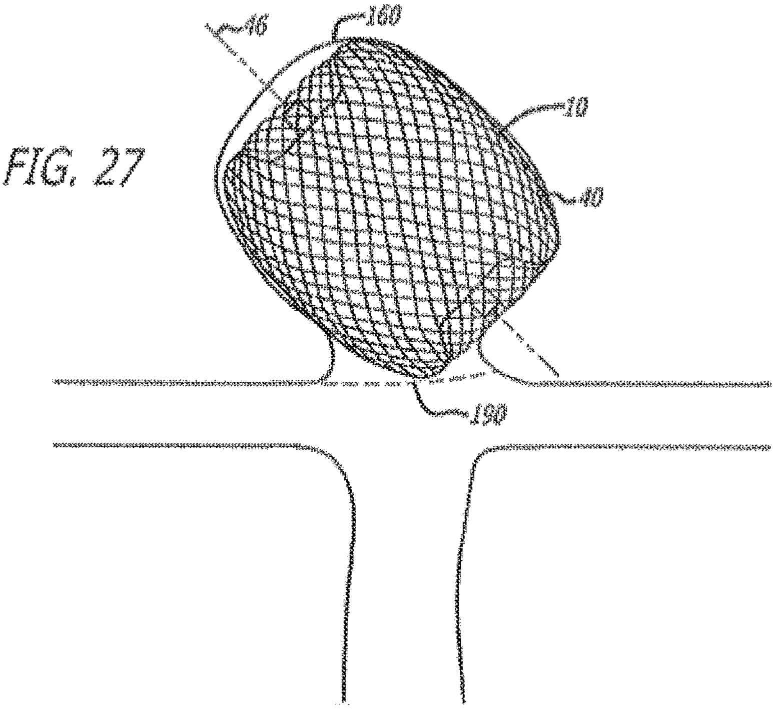
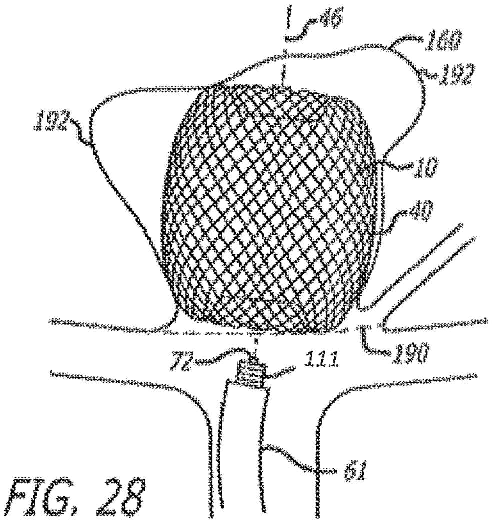
FIG. 28

FILAMENTARY DEVICES FOR TREATMENT OF VASCULAR DEFECTS

CROSS-REFERENCE TO RELATED APPLICATIONS

This application is a continuation of U.S. application Ser. No. 16/815,911, filed Mar. 11, 2020, which claims the benefit of priority under 35 U.S.C. § 119(e) from U.S. Provisional Application Ser. No. 62/873,256, filed Jul. 12, 2019, all of which are hereby expressly incorporated by reference in their entireties for all purposes.

STATEMENT REGARDING FEDERALLY SPONSORED RESEARCH OR DEVELOPMENT

Not applicable.

FIELD OF THE INVENTION

Embodiments of devices and methods herein are directed to blocking a flow of fluid through a tubular vessel or into a small interior chamber of a saccular cavity or vascular defect within a mammalian body. More specifically, embodiments herein are directed to devices and methods for treatment of a vascular defect of a patient including some embodiments directed specifically to the treatment of cerebral aneurysms of patients.

BACKGROUND

The mammalian circulatory system is comprised of a heart, which acts as a pump, and a system of blood vessels which transport the blood to various points in the body. Due to the force exerted by the flowing blood on the blood vessel the blood vessels may develop a variety of vascular defects. One common vascular defect known as an aneurysm results from the abnormal widening of the blood vessel. Typically, vascular aneurysms are formed as a result of the weakening of the wall of a blood vessel and subsequent ballooning and expansion of the vessel wall. If, for example, an aneurysm is present within an artery of the brain, and the aneurysm should burst with resulting cranial hemorrhaging, death could occur.

Surgical techniques for the treatment of cerebral aneurysms typically involve a craniotomy requiring creation of an opening in the skull of the patient through which the surgeon can insert instruments to operate directly on the patient's brain. For some surgical approaches, the brain must be retracted to expose the parent blood vessel from which the aneurysm arises. Once access to the aneurysm is gained, the surgeon places a clip across the neck of the aneurysm thereby preventing arterial blood from entering the aneurysm. Upon correct placement of the clip the aneurysm will be obliterated in a matter of minutes. Surgical techniques may be effective treatment for many aneurysms. Unfortunately, surgical techniques for treating these types of conditions include major invasive surgical procedures which often require extended periods of time under anesthesia involving high risk to the patient. Such procedures thus require that the patient be in generally good physical condition in order to be a candidate for such procedures.

Various alternative and less invasive procedures have been used to treat cerebral aneurysms without resorting to major surgery. One approach to treating aneurysms without the need for invasive surgery involves the placement of sleeves or stents into the vessel and across the region where the aneurysm occurs. Such devices maintain blood flow through the vessel while reducing blood pressure applied to the interior of the aneurysm. Certain types of stents are expanded to the proper size by inflating a balloon catheter, referred to as balloon expandable stents, while other stents are designed to elastically expand in a self-expanding manner. Some stents are covered typically with a sleeve of polymeric material called a graft to form a stent-graft. Stents and stent-grafts are generally delivered to a preselected position adjacent a vascular defect through a delivery catheter. In the treatment of cerebral aneurysms, covered stents or stent-grafts have seen very limited use due to the likelihood of inadvertent occlusion of small perforator vessels that may be near the vascular defect being treated.

In addition, current uncovered stents are generally not sufficient as a stand-alone treatment. In order for stents to fit through the microcatheters used in small cerebral blood vessels, their density is usually reduced such that when expanded there is only a small amount of stent structure bridging the aneurysm neck. Thus, they do not block enough flow to cause clotting of the blood in the aneurysm and are thus generally used in combination with vaso-occlusive devices, such as the coils discussed above, to achieve aneurysm occlusion.

Some procedures involve the delivery of embolic or filling materials into an aneurysm. The delivery of such vaso-occlusion devices or materials may be used to promote hemostasis or fill an aneurysm cavity entirely. Vaso-occlusion devices may be placed within the vasculature of the human body, typically via a catheter, either to block the flow of blood through a vessel with an aneurysm through the formation of an embolus or to form such an embolus within an aneurysm stemming from the vessel. A variety of implantable, coil-type vaso-occlusion devices are known. The coils of such devices may themselves be formed into a secondary coil shape, or any of a variety of more complex secondary shapes. Vaso-occlusive coils are commonly used to treat cerebral aneurysms but suffer from several limitations including poor packing density, compaction due to hydrodynamic pressure from blood flow, poor stability in wide-necked aneurysms, and complexity and difficulty in the deployment thereof as most aneurysm treatments with this approach require the deployment of multiple coils. Coiling is less effective at treating certain physiological conditions, such as wide neck cavities (e.g. wide neck aneurysms) because there is a greater risk of the coils migrating out of the treatment site.

A number of aneurysm neck bridging devices with defect spanning portions or regions have been attempted, however, none of these devices have had a significant measure of clinical success or usage. A major limitation in their adoption and clinical usefulness is the inability to position the defect spanning portion to assure coverage of the neck. Existing stent delivery systems that are neurovascular compatible (i.e. deliverable through a microcatheter and highly flexible) do not have the necessary rotational positioning capability. Another limitation of many aneurysm bridging devices described in the prior art is the poor flexibility. Cerebral blood vessels are tortuous, and a high degree of flexibility is required for effective delivery to most aneurysm locations in the brain.

What has been needed are devices and methods for delivery and use in small and tortuous blood vessels that can substantially block the flow of blood into an aneurysm, such as a cerebral aneurysm, with a decreased risk of inadvertent aneurysm rupture or blood vessel wall damage. In addition, what has been needed are methods and devices suitable for blocking blood flow in cerebral aneurysms over an extended period of time without a significant risk of deformation, compaction or dislocation.

Intrasaccular occlusive devices are part of a newer type of occlusion device used to treat various intravascular conditions including aneurysms. They are often more effective at treating these wide neck conditions, or larger treatment areas. The intrasaccular devices comprise a structure which sits within the aneurysm and provides an occlusive effect at the neck of the aneurysm to help limit blood flow into the aneurysm. The rest of the device comprises a relatively conformable structure that sits within the aneurysm helping to occlude all or a portion of the aneurysm. Intrasaccular devices typically conform to the shape of the treatment site. These devices also occlude the cross section of the neck of the treatment site/aneurysm, thereby promoting clotting and causing thrombosis and closing of the aneurysm over time.

These intrasaccular devices are difficult to design for various reasons. For neurovascular aneurysms, these intrasaccular devices are particularly small and any projecting structures from the intrasaccular device can prod into the vessel or tissue, causing additional complications. In larger aneurysms, there is a risk of compaction where the intrasaccular device can migrate into the aneurysm and leave the neck region. There is a need for an intrasaccular device that addresses these issues.

SUMMARY

An intrasaccular occlusion device is described that is used to treat a variety of conditions, including aneurysms and neurovascular aneurysms. For intrasaccular devices, it is often beneficial to have good flow disruption at the neck of the aneurysm to limit the flow of blood into the aneurysm, good proximal stiffness to augment proximal anchoring retention and reduce the risk of device migration during treatment, and good ability to conform to a shape of a treatment site to augment the occlusive benefit of the device. The following embodiments described and presented herein utilize one or more of these factors in order to increase the effectiveness of an intrasaccular device.

In one embodiment, the occlusion device comprises a mesh of braided wires where the mesh of braided wires is gathered into retention structures at the proximal and distal ends of the device. The retention structure at the distal end of the device projects inwardly within the occlusion device so as to not project outwardly from the device.

In one embodiment, the retention structure comprises a hub or marker band where the wires are attached to the retention structure so as to provide a fixed meeting point for the ends of the wires.

In one embodiment, the distal retention structure is recessed within the distal part of the occlusion device and the distal ends of the wires are attached to the distal retention structure so as to form a distal recess comprised of a distal portion of the wires.

In one embodiment, a multiple layer occlusion device is described. A first layer comprises the length of the occlusion device and a second layer comprises only a proximal section of the occlusion device so as to augment the flow-disruptive and/or occlusive effect along the proximal section of the device. The first layer utilizes a distal retention structure that projects inwardly within the occlusion device and the wires comprising the first layer are attached to the distal retention structure.

In one embodiment, a multiple layer occlusion device is described. A first layer comprises the length of the occlusion device and a second layer comprises only a proximal section of the occlusion device so as to augment the flow-disruptive and/or occlusive effect along the proximal section of the device. The proximal, dual layer portion of the device has a variable height so as to customize the portion of the occlusion device having the augmented occlusive effect.

In one embodiment, a multiple layer occlusion device is described. A first layer comprises the length of the occlusion device and a second layer comprises only a proximal section of the occlusion device so as to augment the flow-disruptive and/or occlusive effect along the proximal section of the device. There is a distal retention structure near the distal end of the device, a proximal retention structure near a proximal end of the device, and a third retention structure binding the distal portion of the secondary augmented occlusion layer. The distal retention structure and the third retention structure are connected to allow the occlusive device height to vary based on the geometry of the treated vascular condition.

In one embodiment, a multiple layer occlusion device is described. A first layer comprises the length of the occlusion device and a second layer comprises only a proximal section of the occlusion device so as to augment the flow-disruptive and/or occlusive effect along the proximal section of the device. In one embodiment, the second layer is a secondary mesh. In one embodiment, the secondary layer is a skeletal wire structure to provide radial stiffness along the proximal portion of the occlusion device.

In another embodiment, a device for treatment of a patient's cerebral aneurysm is described. The device includes a first permeable shell including a radially constrained elongated state configured for delivery within a catheter lumen, an expanded state, and a plurality of elongate filaments that are woven together to form a mesh, the expanded state having a proximal portion, a distal portion, and an interior cavity, wherein each of the plurality of filaments has a proximal end and a distal end, wherein the proximal ends of each of the plurality of filaments are gathered in a proximal hub or marker band and the distal ends of each of the plurality of filaments are gathered by a first distal hub or marker band that is located in the interior cavity; and a second permeable shell including a radially constrained elongated state configured for delivery within a catheter lumen, an expanded state, and a plurality of elongate filaments that are woven together to form a mesh, wherein at least a portion of the second permeable shell is in contact with the proximal portion of the first permeable shell, wherein each of the plurality of filaments of the second permeable shell has a proximal end and a distal end, wherein the distal ends of each of the plurality of filaments of the second permeable shell are gathered in a second distal hub or marker band, and wherein the proximal ends of each of the plurality of filaments of the second permeable shell are gathered in the proximal hub or marker band with the proximal ends of each of the plurality of filaments of the first permeable shell. A length of the expanded state of the second permeable shell is smaller than a length of the expanded state of the first permeable shell. In one embodiment, the first and second distal hubs or marker bands may be coupled together.

In another embodiment, a method for treating a cerebral aneurysm having an interior cavity and a neck is described. The method includes the step of advancing an implant in a microcatheter to a region of interest in a cerebral artery, wherein the implant comprises a first permeable shell including a radially constrained elongated state configured for delivery within a lumen of the microcatheter, an expanded state, and a plurality of elongate filaments that are woven together to form a mesh, the expanded state having a proximal portion, a distal portion, an dan interior cavity, wherein each of the plurality of filaments has a proximal end and a distal end, wherein the proximal ends of each of the plurality of filaments are gathered in a proximal hub or marker band and the distal ends of each of the plurality of filaments are gathered by a first distal hub or marker band located in the interior cavity of the first permeable shell; and a second permeable shell including a radially constrained elongated state configured for delivery within the lumen of the microcatheter, an expanded state, and a plurality of elongate filaments that are woven together to form a mesh, wherein at least a portion of the second permeable shell is in contact with the proximal portion of the first permeable shell, wherein each of the plurality of filaments has a proximal end and a distal end, wherein the distal ends of each of the plurality of filaments of the second permeable shell are gathered in a second distal hub or marker band, and wherein the proximal ends of each of the plurality of filaments of the second permeable shell are gathered in the proximal hub or marker band with the proximal ends of each of the plurality of filaments of the first permeable shell. A length of the expanded state of the second permeable shell is smaller than a length of the expanded state of the first permeable shell. The implant is then deployed within the cerebral aneurysm, wherein the first and second permeable shells expand to each of their expanded states in the interior cavity of the aneurysm. The microcatheter is then withdrawn from the region of interest after deploying the implant.

In another embodiment, a device for treatment of a patient's cerebral aneurysm is described. The device includes a first permeable shell including a radially constrained elongated state configured for delivery within a catheter lumen, an expanded state, and a plurality of elongate filaments that are woven together to form a mesh, the expanded state having a proximal portion, a distal portion, and an interior cavity, wherein each of the plurality of filaments has a proximal end and a distal end, wherein the proximal ends of each of the plurality of filaments are gathered in a proximal hub or marker band and the distal ends of each of the plurality of filaments are gathered by a first distal hub or marker band that is located in the interior cavity; and a second permeable shell including a radially constrained elongated state configured for delivery within a catheter lumen, an expanded state, and a plurality of elongate filaments that are woven together to form a mesh, wherein each of the plurality of filaments of the second permeable shell has a proximal end and a distal end, wherein the distal ends of each of the plurality of filaments of the second permeable shell are gathered in a second distal hub or marker band, and wherein the proximal ends of each of the plurality of filaments of the second permeable shell are gathered in the proximal hub or marker band with the proximal ends of each of the plurality of filaments of the first permeable shell. The first distal hub or marker band and the second distal hub or marker band are coupled together.

In another embodiment, a method for treating a cerebral aneurysm having an interior cavity and a neck is described. The method includes the step of advancing an implant in a microcatheter to a region of interest in a cerebral artery, wherein the implant comprises a first permeable shell including a radially constrained elongated state configured for delivery within a catheter lumen, an expanded state, and a plurality of elongate filaments that are woven together to form a mesh, the expanded state having a proximal portion, a distal portion, and an interior cavity, wherein each of the plurality of filaments has a proximal end and a distal end, wherein the proximal ends of each of the plurality of filaments are gathered in a proximal hub or marker band and the distal ends of each of the plurality of filaments are gathered by a first distal hub or marker band that is located in the interior cavity; and a second permeable shell including a radially constrained elongated state configured for delivery within a catheter lumen, an expanded state, and a plurality of elongate filaments that are woven together to form a mesh, wherein each of the plurality of filaments of the second permeable shell has a proximal end and a distal end, wherein the distal ends of each of the plurality of filaments of the second permeable shell are gathered in a second distal hub or marker band, and wherein the proximal ends of each of the plurality of filaments of the second permeable shell are gathered in the proximal hub or marker band with the proximal ends of each of the plurality of filaments of the first permeable shell. The first distal hub or marker band and the second distal hub or marker band are coupled together. The implant is then deployed within the cerebral aneurysm, wherein the first and second permeable shells expand to each of their expanded states in the interior cavity of the aneurysm. The microcatheter is then withdrawn from the region of interest after deploying the implant.

In any of the embodiments described, the first permeable shell may be less stiff or softer than the second permeable shell such that the distal portion of the device has a soft, deformable distal end and distal region. The filaments making up the first permeable shell may have a smaller diameter than the filaments making up the second permeable shell. The filaments making up the first permeable shell may have a diameter of between about 0.0003" and about 0.00075." The filaments making up the second permeable shell may have a diameter of between about 0.0015" and about 0.004." The first permeable shell may be made from a larger number of filaments woven tighter than the second permeable shell. The first permeable shell may be made from about 36 to about 360 filaments woven together. The second permeable shell may be made from about 4 to about 48 filaments woven together.

In any of the embodiments described, the first permeable shell may have an inverted distal end. The filaments woven together to form the first permeable shell each have a proximal and distal end. The filaments extend from a proximal end to a distal end of the first permeable shell and further extends proximally back towards the proximal end of the first permeable shell, such that the distal ends of each of the plurality of filaments of the first permeable shell are located in the interior cavity of the first permeable shell and the band holding the distal ends of the filaments together is located in the interior cavity of the first permeable shell. The distal hub or marker band of the first permeable shell may be coupled to the distal hub or marker band of the second permeable shell. The distal hubs or marker bands may be coupled together through a tether, wire, or mesh. The proximal and distal hubs or marker bands may be tubular bands.

In any of the embodiments described, the second permeable shell may sit in the proximal section of the device. The second permeable shell may sit in an interior cavity of the first permeable shell such that at least a portion of the outer surface of the second permeable shell is in contact with the inner surface of a proximal section of the first permeable shell. The second permeable shell may be attached to the first permeable shell by welding, adhesive, or mechanical ties. The second permeable shell may be attached to the first permeable shell through the proximal hub or marker band. The proximal ends of the filaments of the second permeable shell and the proximal ends of the filaments of the first permeable shell may all be gathered together in a single hub or marker band.

In any of the embodiments described, the length of the expanded state of the second permeable shell may be between about 10% and about 70%, alternatively between about 10% and about 60%, alternatively between about 10% and about 50%, alternatively between about 10% and about 40%, alternatively between about 10% and about 30% of the length of the expanded state of the first permeable shell.

In another embodiment, a device for treatment of a patient's cerebral aneurysm is described. The device includes a first permeable shell including a first end, a second end, a radially constrained elongated state configured for delivery within a catheter lumen, an expanded state, and a plurality of filaments that are woven together to form a mesh, wherein each of the plurality of filaments has a first end and a second end, wherein each of the plurality of filaments starts at the first end of the first permeable shell, extends to the second end of the first permeable shell, and extends back to the first end of the first permeable shell, and wherein the first and second ends of each of the plurality of filaments are gathered in a hub or marker band at the first end of the first permeable shell; and a scaffolding structure including a radially constrained elongated state configured for delivery within a catheter lumen, an expanded state, and a plurality of scaffolding filaments that are associated with a portion of the first permeable shell that includes the first end of the first permeable shell. In one embodiment, each of the plurality of scaffolding filaments has a diameter that is larger than a diameter of each of the plurality of elongate filaments of the first permeable shell.

In another embodiment, a method for treating a cerebral aneurysm having an interior cavity and a neck is described. The method includes the step of advancing an implant in a microcatheter to a region of interest in a cerebral artery, wherein the implant comprises a first permeable shell including a first end, a second end, a radially constrained elongated state configured for delivery within a lumen of the microcatheter, an expanded state, and a plurality of filaments that are woven together to form a mesh, wherein each of the plurality of filaments has a first end and a second end, wherein each of the plurality of filaments starts at the first end of the first permeable shell, extends to the second end of the first permeable shell, and extends back to the first end of the first permeable shell, and wherein the first and second ends of each of the plurality of filaments are gathered in a hub or marker band at the first end of the first permeable shell; and a scaffolding structure including a radially constrained elongated state configured for delivery within the lumen of the microcatheter, an expanded state, and a plurality of scaffolding filaments that are associated with a portion of the first permeable shell that includes the first end of the first permeable shell. In one embodiment, each of the plurality of scaffolding filaments has a diameter that is larger than a diameter of each of the plurality of filaments of the first permeable shell. The implant is then deployed within the cerebral aneurysm, wherein the permeable shell and the scaffolding structure expand to each of their expanded states in the interior cavity of the aneurysm. The microcatheter is then withdrawn from the region of interest after deploying the implant.

In any of the embodiments described, the scaffolding structure is coupled to the first permeable shell. The scaffolding structure may be coupled to the first permeable shell using welding, adhesive, or mechanical ties. The plurality of scaffolding filaments of the scaffolding structure may be woven into the mesh of the first permeable shell.

In any of the embodiments described, the scaffolding filaments may have a diameter of between about 0.001" and about 0.004". The scaffolding filaments may be made from a shape memory alloy such as nitinol, or DFT, or combinations thereof. The expanded state of the scaffolding structure may have a scalloped shaped open distal end wherein the scaffolding wires extend distally from a proximal end and curve back in a proximal direction to form a curved shape in a distal region. Adjacent scaffolding filaments may be connected together to form the scalloped shape open distal end.

In any of the embodiments described, the scaffolding structure has a height between about 10% and about 70% of the height of the first permeable shell.

In any of the embodiments described, the portion of the device that includes the scaffolding structure is stiffer than the portion of the device near the distal end that does not include the scaffolding structure. The portion of the device that includes the scaffolding structure may have a stiffness of at least about 0.001 N/mm. The distal portion of the device that does not include the scaffolding structure may have a stiffness or no more than about 0.020 N/mm.

In any of the embodiments described, both of the permeable shell and the scaffolding structure are self-expandable.

In any of the embodiments described, the permeable shell may have an inverted distal end. The filaments woven together to form the permeable shell each have a proximal and distal end. The distal end of the filaments extend from a proximal end to a distal end of the permeable shell and further extends proximally back to the proximal end of the permeable shell, such that the proximal and distal ends of each of the plurality of filaments of the permeable shell are gathered together in a band at the proximal end of the permeable shell. Thus, the device has a cavity (e.g., a conical shaped cavity or a cylindrical shaped cavity), extending from the distal end and terminating at the proximal band at the proximal end of the permeable shell.

BRIEF DESCRIPTION OF THE DRAWINGS

FIGS. 23-26 show a deployment sequence of a device for treatment of a patient's vasculature.

FIG. 27 is an elevation view in partial section of an embodiment of a device for treatment of a patient's vasculature deployed within an aneurysm at a tilted angle.

FIG. 28 is an elevation view in partial section of an embodiment of a device for treatment of a patient's vasculature deployed within an irregularly shaped aneurysm.

DETAILED DESCRIPTION

Figure 1:
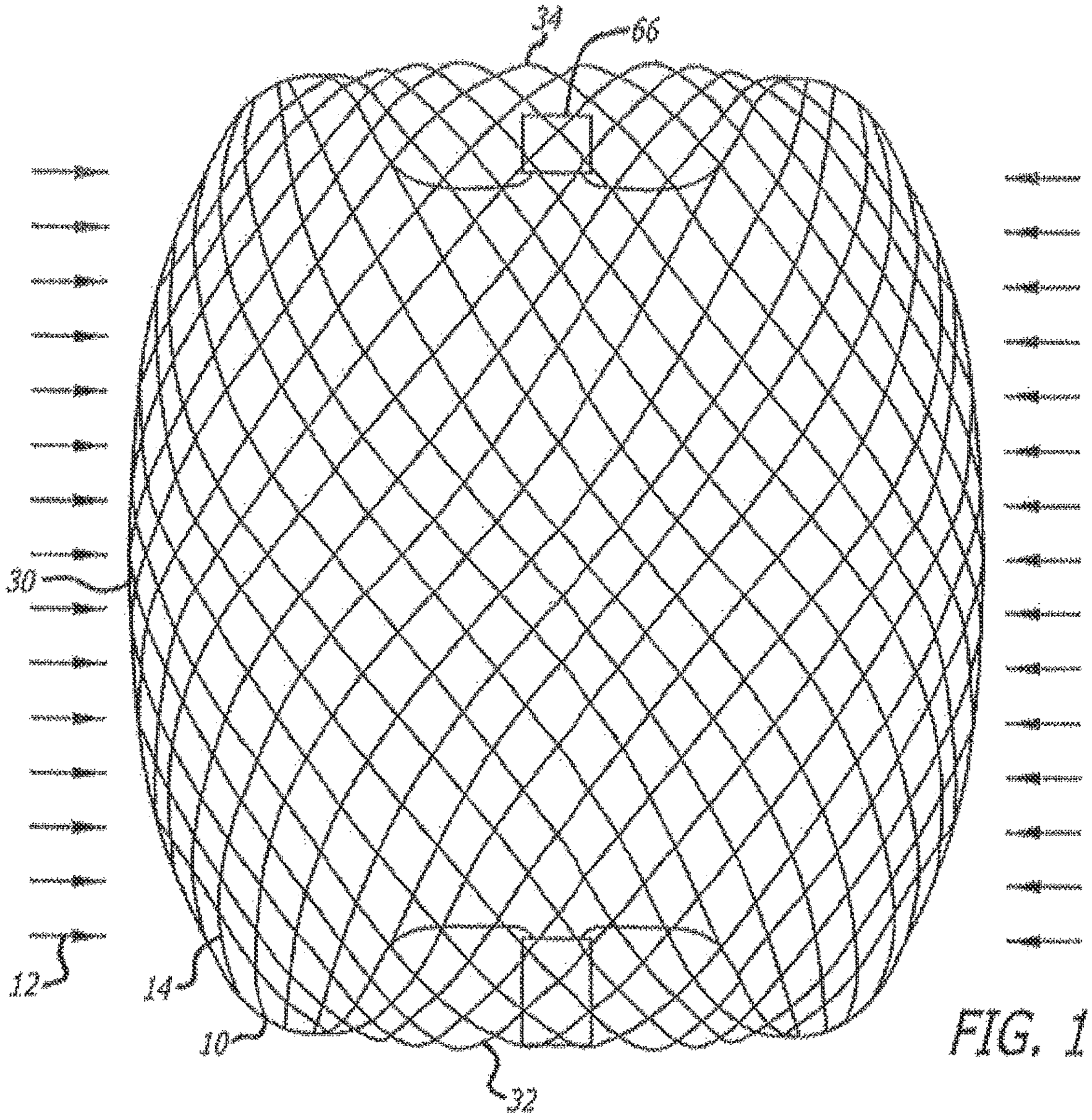
FIG. 1 is an elevation view of an embodiment of a device for treatment of a patient's vasculature and a plurality of arrows indicating inward radial force.

Discussed herein are devices and methods for the treatment of vascular defects that are suitable for minimally invasive deployment within a patient's vasculature, and particularly, within the cerebral vasculature of a patient. For such embodiments to be safely and effectively delivered to a desired treatment site and effectively deployed, some device embodiments may be configured for collapse to a low profile constrained state with a transverse dimension suitable for delivery through an inner lumen of a microcatheter and deployment from a distal end thereof. Embodiments of these devices may also maintain a clinically effective configuration with sufficient mechanical integrity once deployed so as to withstand dynamic forces within a patient's vasculature over time that may otherwise result in compaction of a deployed device. It may also be desirable for some device embodiments to acutely occlude a vascular defect of a patient during the course of a procedure in order to provide more immediate feedback regarding success of the treatment to a treating physician.

Intrasaccular occlusive devices that include a permeable shell formed from a woven or braided mesh have been described in US 2017/0095254, US 2016/0249934, US 2016/0367260, US 2016/0249937, and US 2018/0000489, all of which are hereby expressly incorporated by reference in their entirety for all purposes.

Some embodiments are particularly useful for the treatment of cerebral aneurysms by reconstructing a vascular wall so as to wholly or partially isolate a vascular defect from a patient's blood flow. Some embodiments may be configured to be deployed within a vascular defect to facilitate reconstruction, bridging of a vessel wall or both in order to treat the vascular defect. For some of these embodiments, the permeable shell of the device may be configured to anchor or fix the permeable shell in a clinically beneficial position. For some embodiments, the device may be disposed in whole or in part within the vascular defect in order to anchor or fix the device with respect to the vascular structure or defect. The permeable shell may be configured to span an opening, neck or other portion of a vascular defect in order to isolate the vascular defect, or a portion thereof, from the patient's nominal vascular system in order allow the defect to heal or to otherwise minimize the risk of the defect to the patient's health.

For some or all of the embodiments of devices for treatment of a patient's vasculature discussed herein, the permeable shell may be configured to allow some initial perfusion of blood through the permeable shell. The porosity of the permeable shell may be configured to sufficiently isolate the vascular defect so as to promote healing and isolation of the defect, but allow sufficient initial flow through the permeable shell so as to reduce or otherwise minimize the mechanical force exerted on the membrane the dynamic flow of blood or other fluids within the vasculature against the device. For some embodiments of devices for treatment of a patient's vasculature, only a portion of the permeable shell that spans the opening or neck of the vascular defect, sometimes referred to as a defect spanning portion, need be permeable and/or conducive to thrombus formation in a patient's bloodstream. For such embodiments, that portion of the device that does not span an opening or neck of the vascular defect may be substantially non-permeable or completely permeable with a pore or opening configuration that is too large to effectively promote thrombus formation.

In general, it may be desirable in some cases to use a hollow, thin walled device with a permeable shell of resilient material that may be constrained to a low profile for delivery within a patient. Such a device may also be configured to expand radially outward upon removal of the constraint such that the shell of the device assumes a larger volume and fills or otherwise occludes a vascular defect within which it is deployed. The outward radial expansion of the shell may serve to engage some or all of an inner surface of the vascular defect whereby mechanical friction between an outer surface of the permeable shell of the device and the inside surface of the vascular defect effectively anchors the device within the vascular defect. Some embodiments of such a device may also be partially or wholly mechanically captured within a cavity of a vascular defect, particularly where the defect has a narrow neck portion with a larger interior volume. In order to achieve a low profile and volume for delivery and be capable of a high ratio of expansion by volume, some device embodiments include a matrix of woven or braided filaments that are coupled together by the interwoven structure so as to form a self-expanding permeable shell having a pore or opening pattern between couplings or intersections of the filaments that is substantially regularly spaced and stable, while still allowing for conformity and volumetric constraint.

As used herein, the terms woven and braided are used interchangeably to mean any form of interlacing of filaments to form a mesh structure. In the textile and other industries, these terms may have different or more specific meanings depending on the product or application such as whether an article is made in a sheet or cylindrical form. For purposes of the present disclosure, these terms are used interchangeably.

For some embodiments, three factors may be critical for a woven or braided wire occlusion device for treatment of a patient's vasculature that can achieve a desired clinical outcome in the endovascular treatment of cerebral aneurysms. We have found that for effective use in some applications, it may be desirable for the implant device to have sufficient radial stiffness for stability, limited pore size for near-complete acute (intra-procedural) occlusion and a collapsed profile which is small enough to allow insertion through an inner lumen of a microcatheter. A device with a radial stiffness below a certain threshold may be unstable and may be at higher risk of embolization in some cases. Larger pores between filament intersections in a braided or woven structure may not generate thrombus and occlude a vascular defect in an acute setting and thus may not give a treating physician or health professional such clinical feedback that the flow disruption will lead to a complete and lasting occlusion of the vascular defect being treated. Delivery of a device for treatment of a patient's vasculature through a standard microcatheter may be highly desirable to allow access through the tortuous cerebral vasculature in the manner that a treating physician is accustomed. A detailed discussion of radial stiffness, pore size, and the necessary collapsed profile can be found in US 2017/0095254, which was previously expressly incorporated by reference in its entirety.

As has been discussed, some embodiments of devices for treatment of a patient's vasculature call for sizing the device which approximates (or with some over-sizing) the vascular site dimensions to fill the vascular site. One might assume that scaling of a device to larger dimensions and using larger filaments would suffice for such larger embodiments of a device. However, for the treatment of brain aneurysms, the diameter or profile of the radially collapsed device is limited by the catheter sizes that can be effectively navigated within the small, tortuous vessels of the brain. Further, as a device is made larger with a given or fixed number of resilient filaments having a given size or thickness, the pores or openings between junctions of the filaments are correspondingly larger. In addition, for a given filament size the flexural modulus or stiffness of the filaments and thus the structure decrease with increasing device dimension. Flexural modulus may be defined as the ratio of stress to strain. Thus, a device may be considered to have a high flexural modulus or be stiff if the strain (deflection) is low under a given force. A stiff device may also be said to have low compliance.

To properly configure larger size devices for treatment of a patient's vasculature, it may be useful to model the force on a device when the device is deployed into a vascular site or defect, such as a blood vessel or aneurysm, that has a diameter or transverse dimension that is smaller than a nominal diameter or transverse dimension of the device in a relaxed unconstrained state. As discussed, it may be advisable to "over-size" the device in some cases so that there is a residual force between an outside surface of the device and an inside surface of the vascular wall. The inward radial force on a device 10 that results from over-sizing is illustrated schematically in FIG. 1 with the arrows 12 in the figure representing the inward radial force. As shown in FIG. 2, these compressive forces on the filaments 14 of the device in FIG. 1 can be modeled as a simply supported beam 16 with a distributed load or force as show by the arrows 18 in the figure. It can be seen from the equation below for the deflection of a beam with two simple supports 20 and a distributed load that the deflection is a function of the length, L to the $4^{th}$ power:

$$\text{Deflection of Beam}=5FL^4/384\ El$$

where F=force,

L=length of beam,

E=Young's Modulus, and l=moment of inertia.

Thus, as the size of the device increases and L increases, the compliance increases substantially. Accordingly, an outward radial force exerted by an outside surface of the filaments 14 of the device 10 against a constraining force when inserted into a vascular site such as blood vessel or aneurysm is lower for a given amount of device compression or over-sizing. This force may be important in some applications to assure device stability and to reduce the risk of migration of the device and potential distal embolization.

In some embodiments, a combination of small and large filament sizes may be utilized to make a device with a desired radial compliance and yet have a collapsed profile which is configured to fit through an inner lumen of commonly used microcatheters. A device fabricated with even a small number of relatively large filaments 14 can provide reduced radial compliance (or increased stiffness) compared to a device made with all small filaments. Even a relatively small number of larger filaments may provide a substantial increase in bending stiffness due to change in the moment of Inertia that results from an increase in diameter without increasing the total cross sectional area of the filaments. The moment of inertia (I) of a round wire or filament may be defined by the equation:

$$I=\pi d^4/64$$

where d is the diameter of the wire or filament.

Since the moment of inertia is a function of filament diameter to the fourth power, a small change in the diameter greatly increases the moment of inertia. Thus, small changes in filament size can have substantial impact on the deflection at a given load and thus the compliance of the device.

Thus, the stiffness can be increased by a significant amount without a large increase in the cross sectional area of a collapsed profile of the device 10. This may be particularly important as device embodiments are made larger to treat large aneurysms. While large cerebral aneurysms may be relatively rare, they present an important therapeutic challenge as some embolic devices currently available to physicians have relatively poor results compared to smaller aneurysms.

As such, some embodiments of devices for treatment of a patient's vasculature may be formed using a combination of filaments 14 with a number of different diameters such as 2, 3, 4, 5 or more different diameters or transverse dimensions. In device embodiments where filaments with two different diameters are used, some larger filament embodiments may have a transverse dimension of about 0.001 inches to about 0.004 inches and some small filament embodiments may have a transverse dimension or diameter of about 0.0004 inches and about 0.0015 inches, more specifically, about 0.0004 inches to about 0.001 inches. The ratio of the number of large filaments to the number of small filaments may be between about 2 and 12 and may also be between about 4 and 8. In some embodiments, the difference in diameter or transverse dimension between the larger and smaller filaments may be less than about 0.004 inches, more specifically, less than about 0.0035 inches, and even more specifically, less than about 0.002 inches.

As discussed above, device embodiments 10 for treatment of a patient's vasculature may include a plurality of wires, fibers, threads, tubes or other filamentary elements that form a structure that serves as a permeable shell. For some embodiments, a globular shape may be formed from such filaments by connecting or securing the ends of a tubular braided structure. For such embodiments, the density of a braided or woven structure may inherently increase at or near the ends where the wires or filaments 14 are brought together and decrease at or near a middle portion 30 disposed between a proximal end 32 and distal end 34 of the permeable shell 40. For some embodiments, an end or any other suitable portion of a permeable shell 40 may be positioned in an opening or neck of a vascular defect such as an aneurysm for treatment. As such, a braided or woven filamentary device with a permeable shell may not require the addition of a separate defect spanning structure having properties different from that of a nominal portion of the permeable shell to achieve hemostasis and occlusion of the vascular defect. Such a filamentary device may be fabricated by braiding, weaving or other suitable filament fabrication techniques. Such device embodiments may be shape set into a variety of three-dimensional shapes such as discussed herein.

Referring to FIGS. 3-10, an embodiment of a device for treatment of a patient's vasculature 10 is shown. The device 10 includes a self-expanding resilient permeable shell 40 having a proximal end 32, a distal end 34, a longitudinal axis 46 and further comprising a plurality of elongate resilient filaments 14 including large filaments 48 and small filaments 50 of at least two different transverse dimensions as shown in more detail in FIGS. 5, 7, and 18. The filaments 14 have a woven structure and are secured relative to each other at proximal ends 60 and distal ends 62 thereof. The permeable shell 40 of the device has a radially constrained elongated state configured for delivery within a microcatheter 61, as shown in FIG. 11, with the thin woven filaments 14 extending longitudinally from the proximal end 42 to the distal end 44 radially adjacent each other along a length of the filaments.

As shown in FIGS. 3-6, the permeable shell 40 also has an expanded relaxed state with a globular and longitudinally shortened configuration relative to the radially constrained state. In the expanded state, the woven filaments 14 form the self-expanding resilient permeable shell 40 in a smooth path radially expanded from a longitudinal axis 46 of the device between the proximal end 32 and distal end 34. The woven structure of the filaments 14 includes a plurality of openings 64 in the permeable shell 40 formed between the woven filaments. For some embodiments, the largest of said openings 64 may be configured to allow blood flow through the openings only at a velocity below a thrombotic threshold velocity. Thrombotic threshold velocity has been defined, at least by some, as the time-average velocity at which more than 50% of a vascular graft surface is covered by thrombus when deployed within a patient's vasculature. In the context of aneurysm occlusion, a slightly different threshold may be appropriate. Accordingly, the thrombotic threshold velocity as used herein shall include the velocity at which clotting occurs within or on a device, such as device 10, deployed within a patient's vasculature such that blood flow into a vascular defect treated by the device is substantially blocked in less than about 1 hour or otherwise during the treatment procedure. The blockage of blood flow into the vascular defect may be indicated in some cases by minimal contrast agent entering the vascular defect after a sufficient amount of contrast agent has been injected into the patient's vasculature upstream of the implant site and visualized as it dissipates from that site. Such sustained blockage of flow within less than about 1 hour or during the duration of the implantation procedure may also be referred to as acute occlusion of the vascular defect.

As such, once the device 10 is deployed, any blood flowing through the permeable shell may be slowed to a velocity below the thrombotic threshold velocity and thrombus will begin to form on and around the openings in the permeable shell 40. Ultimately, this process may be configured to produce acute occlusion of the vascular defect within which the device 10 is deployed. For some embodiments, at least the distal end of the permeable shell 40 may have a reverse bend in an everted configuration such that the secured distal ends 62 of the filaments 14 are withdrawn axially within the nominal permeable shell structure or contour in the expanded state. For some embodiments, the proximal end of the permeable shell further includes a reverse bend in an everted configuration such that the secured proximal ends 60 of the filaments 14 are withdrawn axially within the nominal permeable shell structure 40 in the expanded state. As used herein, the term everted may include a structure that is everted, partially everted and/or recessed with a reverse bend as shown in the device embodiment of FIGS. 3-6. For such embodiments, the ends 60 and 62 of the filaments 14 of the permeable shell or hub structure disposed around the ends may be withdrawn within or below the globular shaped periphery of the permeable shell of the device.

The elongate resilient filaments 14 of the permeable shell 40 may be secured relative to each other at proximal ends 60 and distal ends 62 thereof by one or more methods including welding, soldering, adhesive bonding, epoxy bonding or the like. In addition to the ends of the filaments being secured together, a distal hub 66 may also be secured to the distal ends 62 of the thin filaments 14 of the permeable shell 40 and a proximal hub 68 secured to the proximal ends 60 of the thin filaments 14 of the permeable shell 40. The proximal hub 68 may include a cylindrical member that extends proximally beyond the proximal ends 60 of the thin filaments so as to form a cavity 70 within a proximal portion of the proximal hub 68. The proximal cavity 70 may be used for holding adhesives such as epoxy, solder or any other suitable bonding agent for securing an elongate detachment tether 72 that may in turn be detachably secured to a delivery apparatus such as is shown in FIG. 11.

For some embodiments, the elongate resilient filaments 14 of the permeable shell 40 may have a transverse cross section that is substantially round in shape and be made from a superelastic material that may also be a shape memory metal. The shape memory metal of the filaments of the permeable shell 40 may be heat set in the globular configuration of the relaxed expanded state as shown in FIGS. 3-6. Suitable superelastic shape memory metals may include alloys such as NiTi alloy and the like. The superelastic properties of such alloys may be useful in providing the resilient properties to the elongate filaments 14 so that they can be heat set in the globular form shown, fully constrained for delivery within an inner lumen of a microcatheter and then released to self expand back to substantially the original heat set shape of the globular configuration upon deployment within a patient's body.

The device 10 may have an everted filamentary structure with a permeable shell 40 having a proximal end 32 and a distal end 34 in an expanded relaxed state. The permeable shell 40 has a substantially enclosed configuration for the embodiments shown. Some or all of the permeable shell 40 of the device 10 may be configured to substantially block or impede fluid flow or pressure into a vascular defect or otherwise isolate the vascular defect over some period of time after the device is deployed in an expanded state. The permeable shell 40 and device 10 generally also has a low profile, radially constrained state, as shown in FIG. 11, with an elongated tubular or cylindrical configuration that includes the proximal end 32, the distal end 34 and a longitudinal axis 46. While in the radially constrained state, the elongate flexible filaments 14 of the permeable shell 40 may be disposed substantially parallel and in close lateral proximity to each other between the proximal end and distal end forming a substantially tubular or compressed cylindrical configuration.

Figure 4:
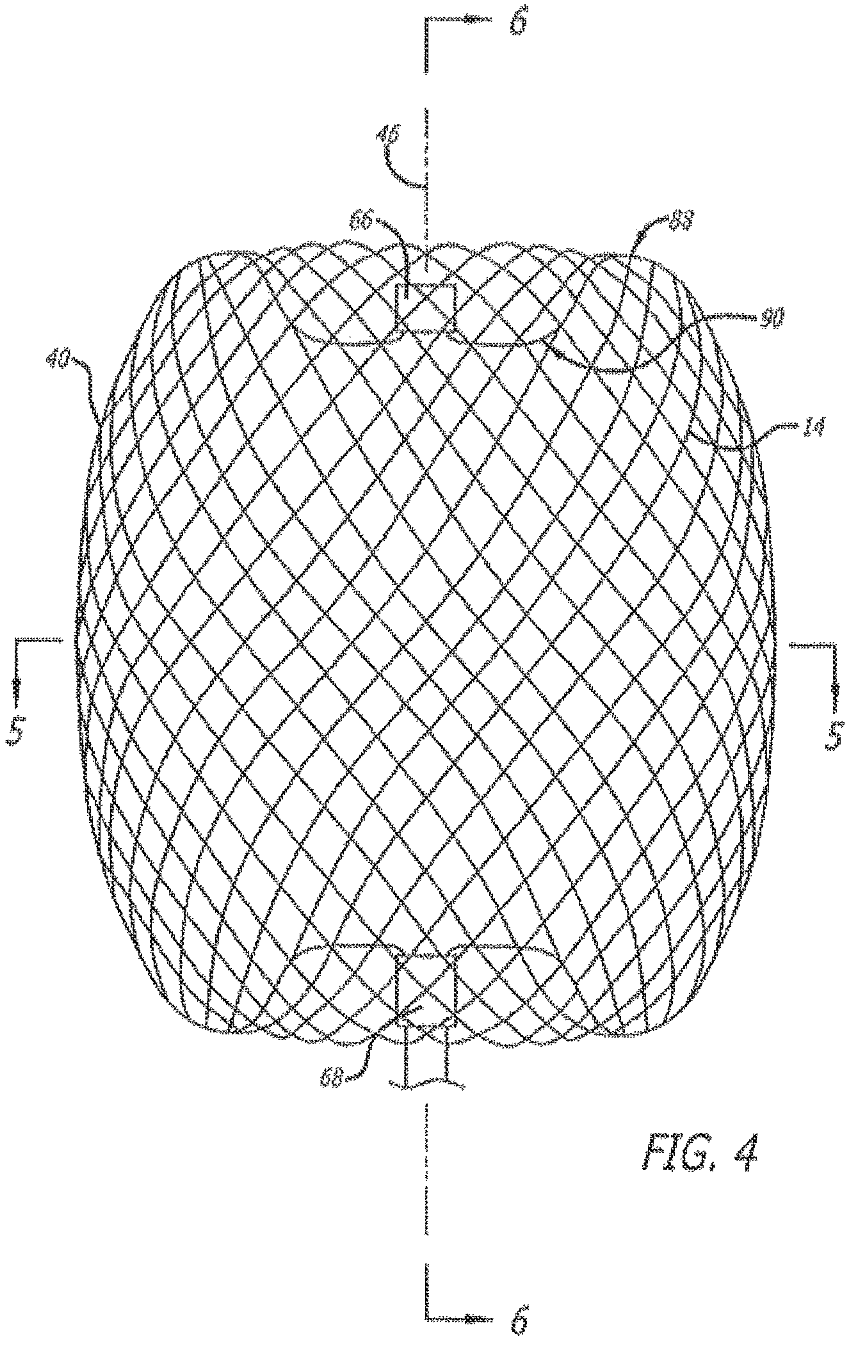
FIG. 4 is an elevation view of the device for treatment of a patient's vasculature of FIG. 3.
Figure 5:
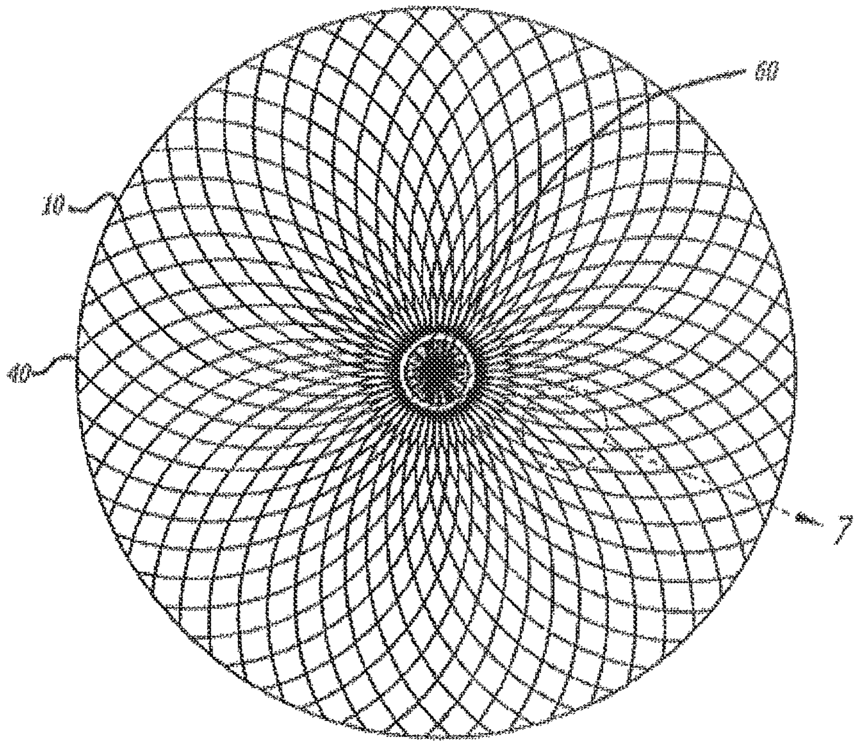
FIG. 5 is a transverse cross-sectional view of the device of FIG. 4 taken along lines 5-5 in FIG. 4.

Proximal ends 60 of at least some of the filaments 14 of the permeable shell 40 may be secured to the proximal hub 68 and distal ends 62 of at least some of the filaments 14 of the permeable shell 40 are secured to the distal hub 66, with the proximal hub 68 and distal hub 66 being disposed substantially concentric to the longitudinal axis 46 as shown in FIG. 4. The ends of the filaments 14 may be secured to the respective hubs 66 and 68 by any of the methods discussed above with respect to securement of the filament ends to each other, including the use of adhesives, solder, welding and the like. A middle portion 30 of the permeable shell 40 may have a first transverse dimension with a low profile suitable for delivery from a microcatheter as shown in FIG. 11. Radial constraint on the device 10 may be applied by an inside surface of the inner lumen of a microcatheter, such as the distal end portion of the microcatheter 61 shown, or it may be applied by any other suitable mechanism that may be released in a controllable manner upon ejection of the device 10 from the distal end of the catheter. In FIG. 11 a proximal end or hub 68 of the device 10 is secured to a distal end of an elongate delivery apparatus 111 of a delivery system 112 disposed at the proximal hub 68 of the device 10. Additional details of delivery devices can be found in, e.g., US 2016/0367260, which was previously incorporated by reference in its entirety.

Some device embodiments 10 having a braided or woven filamentary structure may be formed using about 10 filaments to about 300 filaments 14, more specifically, about 10 filaments to about 100 filaments 14, and even more specifically, about 60 filaments to about 80 filaments 14. Some embodiments of a permeable shell 40 may include about 70 filaments to about 300 filaments extending from the proximal end 32 to the distal end 34, more specifically, about 100 filaments to about 200 filaments extending from the proximal end 32 to the distal end 34. For some embodiments, the filaments 14 may have a transverse dimension or diameter of about 0.0008 inches to about 0.004 inches. The elongate resilient filaments 14 in some cases may have an outer transverse dimension or diameter of about 0.0005 inch to about 0.005 inch, more specifically, about 0.001 inch to about 0.003 inch, and in some cases about 0.0004 inches to about 0.002 inches. For some device embodiments 10 that include filaments 14 of different sizes, the large filaments 48 of the permeable shell 40 may have a transverse dimension or diameter that is about 0.001 inches to about 0.004 inches and the small filaments 50 may have a transverse dimension or diameter of about 0.0004 inches to about 0.0015 inches, more specifically, about 0.0004 inches to about 0.001 inches. In addition, a difference in transverse dimension or diameter between the small filaments 50 and the large filaments 48 may be less than about 0.004 inches, more specifically, less than about 0.0035 inches, and even more specifically, less than about 0.002 inches. For embodiments of permeable shells 40 that include filaments 14 of different sizes, the number of small filaments 50 of the permeable shell 40 relative to the number of large filaments 48 of the permeable shell 40 may be about 2 to 1 to about 15 to 1, more specifically, about 2 to 1 to about 12 to 1, and even more specifically, about 4 to 1 to about 8 to 1.

The expanded relaxed state of the permeable shell 40, as shown in FIG. 4, has an axially shortened configuration relative to the constrained state such that the proximal hub 68 is disposed closer to the distal hub 66 than in the constrained state. Both hubs 66 and 68 are disposed substantially concentric to the longitudinal axis 46 of the device and each filamentary element 14 forms a smooth arc between the proximal and distal hubs 66 and 68 with a reverse bend at each end. A longitudinal spacing between the proximal and distal hubs 66 and 68 of the permeable shell 40 in a deployed relaxed state may be about 25 percent to about 75 percent of the longitudinal spacing between the proximal and distal hubs 66 and 68 in the constrained cylindrical state, for some embodiments. The arc of the filaments 14 between the proximal and distal ends 32 and 34 may be configured such that a middle portion of each filament 14 has a second transverse dimension substantially greater than the first transverse dimension.

For some embodiments, the permeable shell 40 may have a first transverse dimension in a collapsed radially constrained state of about 0.2 mm to about 2 mm and a second transverse dimension in a relaxed expanded state of about 4 mm to about 30 mm. For some embodiments, the second transverse dimension of the permeable shell 40 in an expanded state may be about 2 times to about 150 times the first transverse dimension, more specifically, about 10 times to about 25 times the first or constrained transverse dimension. A longitudinal spacing between the proximal end 32 and distal end 34 of the permeable shell 40 in the relaxed expanded state may be about 25% percent to about 75% percent of the spacing between the proximal end 32 and distal end 34 in the constrained cylindrical state. For some embodiments, a major transverse dimension of the permeable shell 40 in a relaxed expanded state may be about 4 mm to about 30 mm, more specifically, about 9 mm to about 15 mm, and even more specifically, about 4 mm to about 8 mm.

Figure 6:
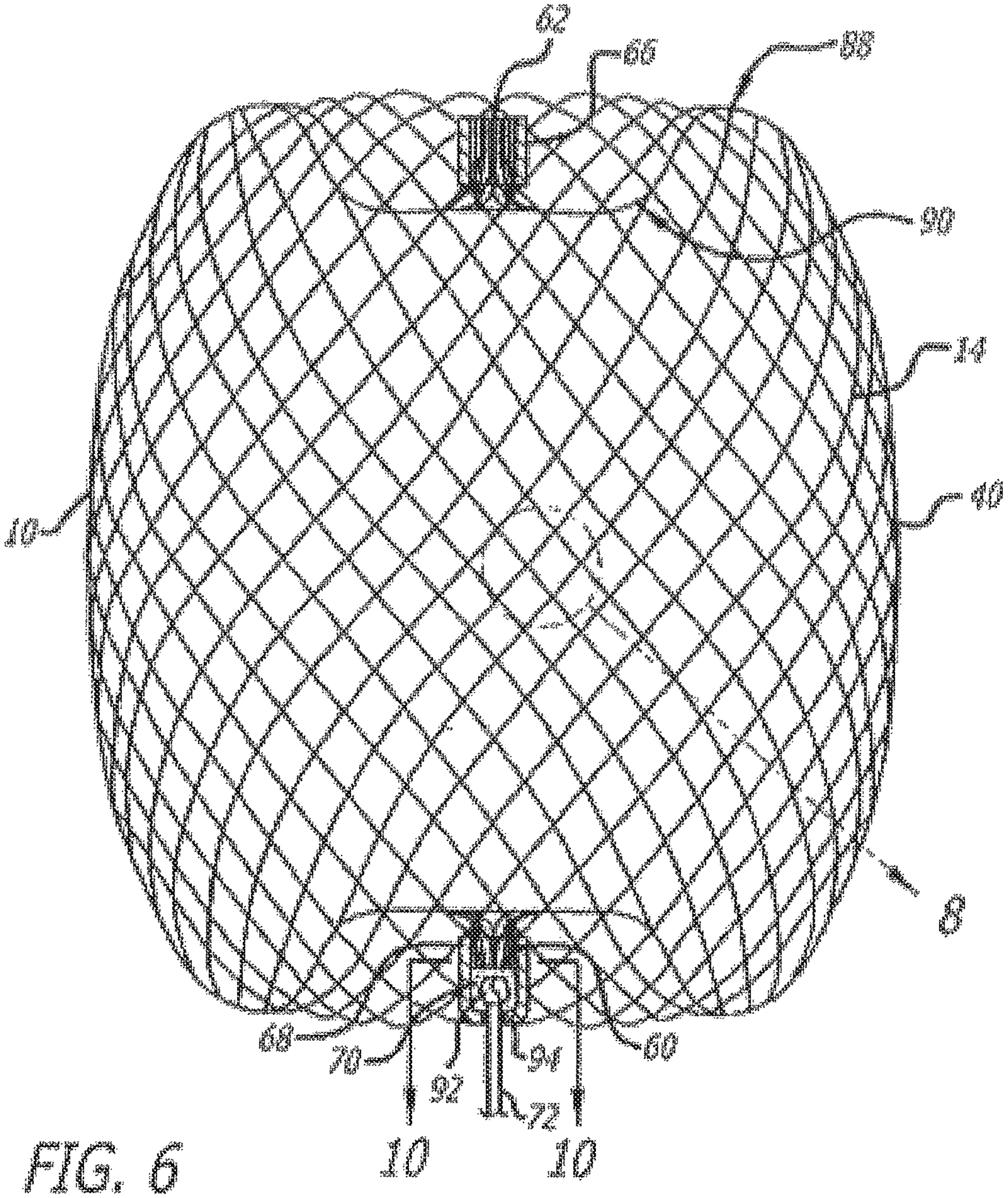
FIG. 6 shows the device of FIG. 4 in longitudinal section taken along lines 6-6 in FIG. 4.

An arced portion of the filaments 14 of the permeable shell 40 may have a sinusoidal-like shape with a first or outer radius 88 and a second or inner radius 90 near the ends of the permeable shell 40 as shown in FIG. 6. This sinusoid-like or multiple curve shape may provide a concavity in the proximal end 32 that may reduce an obstruction of flow in a parent vessel adjacent a vascular defect. For some embodiments, the first radius 88 and second radius 90 of the permeable shell 40 may be between about 0.12 mm to about 3 mm. For some embodiments, the distance between the proximal end 32 and distal end 34 may be less than about 60% of the overall length of the permeable shell 40 for some embodiments. Such a configuration may allow for the distal end 34 to flex downward toward the proximal end 32 when the device 10 meets resistance at the distal end 34 and thus may provide longitudinal conformance. The filaments 14 may be shaped in some embodiments such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. For some embodiments, one of the ends 32 or 34 may be retracted or everted to a greater extent than the other so as to be more longitudinally or axially conformal than the other end.

The first radius 88 and second radius 90 of the permeable shell 40 may be between about 0.12 mm to about 3 mm for some embodiments. For some embodiments, the distance between the proximal end 32 and distal end 34 may be more than about 60% of the overall length of the expanded permeable shell 40. Thus, the largest longitudinal distance between the inner surfaces may be about 60% to about 90% of the longitudinal length of the outer surfaces or the overall length of device 10. A gap between the hubs 66 and 68 at the proximal end 32 and distal end 34 may allow for the distal hub 66 to flex downward toward the proximal hub 68 when the device 10 meets resistance at the distal end and thus provides longitudinal conformance. The filaments 14 may be shaped such that there are no portions that are without curvature over a distance of more than about 2 mm. Thus, for some embodiments, each filament 14 may have a substantially continuous curvature. This substantially continuous curvature may provide smooth deployment and may reduce the risk of vessel perforation. The distal end 34 may be retracted or everted to a greater extent than the proximal end 32 such that the distal end portion of the permeable shell 40 may be more radially conformal than the proximal end portion. Conformability of a distal end portion may provide better device conformance to irregular shaped aneurysms or other vascular defects. A convex surface of the device may flex inward forming a concave surface to conform to curvature of a vascular site.

Figure 10:
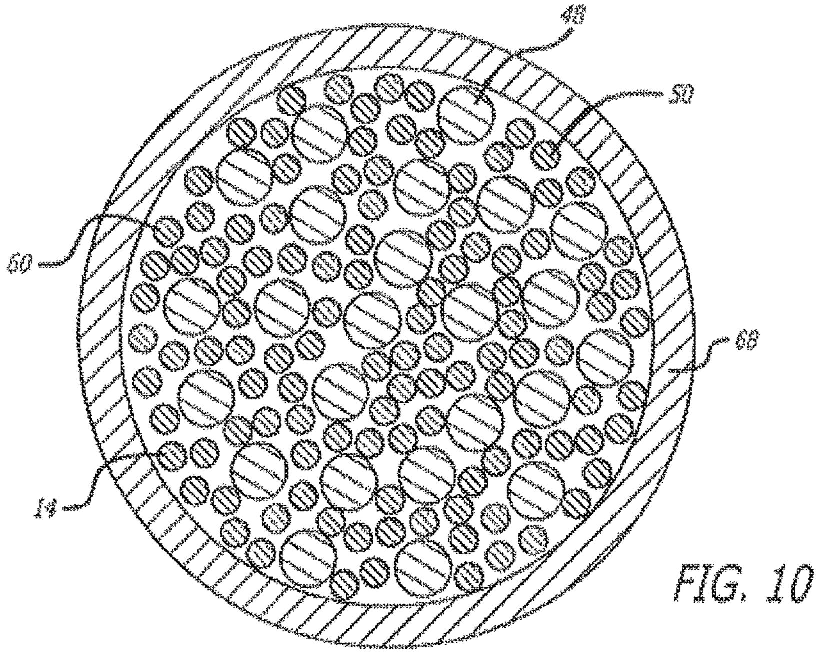
FIG. 10 is a transverse sectional view of a proximal hub portion of the device in FIG. 6 indicated by lines 10-10 in FIG. 6.
Figure 11:
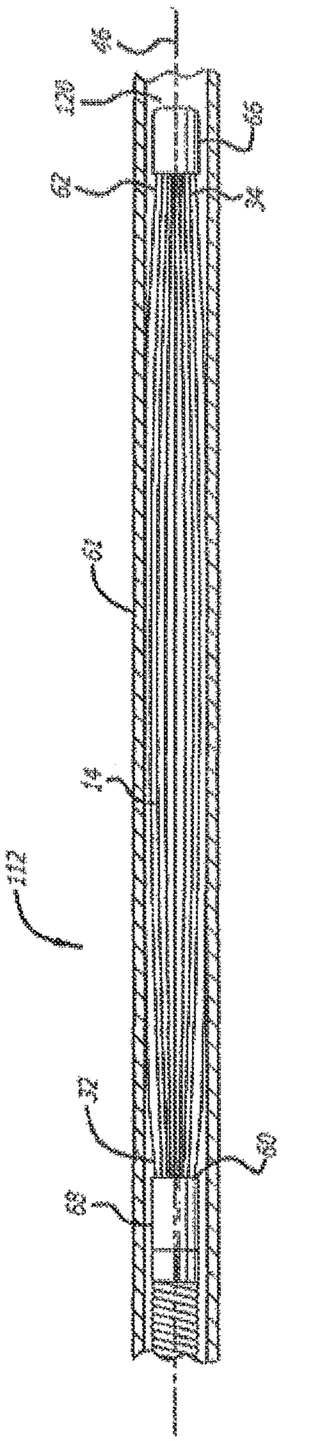
FIG. 11 is an elevation view in partial section of a distal end of a delivery catheter with the device for treatment of a patient's vasculature of FIG. 3 disposed therein in a collapsed constrained state.

FIG. 10 shows an enlarged view of the filaments 14 disposed within a proximal hub 68 of the device 10 with the filaments 14 of two different sizes constrained and tightly packed by an outer ring of the proximal hub 68. The tether member 72 may optionally be disposed within a middle portion of the filaments 14 or within the cavity 70 of the proximal hub 68 proximal of the proximal ends 60 of the filaments 14 as shown in FIG. 6. The distal end of the tether 72 may be secured with a knot 92 formed in the distal end thereof which is mechanically captured in the cavity 70 of the proximal hub 68 formed by a proximal shoulder portion 94 of the proximal hub 68. The knotted distal end 92 of the tether 72 may also be secured by bonding or potting of the distal end of the tether 72 within the cavity 70 and optionally amongst the proximal ends 60 of the filaments 14 with mechanical compression, adhesive bonding, welding, soldering, brazing or the like. The tether embodiment 72 shown in FIG. 6 has a knotted distal end 92 potted in the cavity of the proximal hub 68 with an adhesive. Such a tether 72 may be a dissolvable, severable or releasable tether that may be part of a delivery apparatus 111 used to deploy the device 10 as shown in FIG. 11 and FIGS. 23-26. FIG. 10 also shows the large filaments 48 and small filaments 50 disposed within and constrained by the proximal hub 68 which may be configured to secure the large and small filaments 48 and 50 in place relative to each other within the outer ring of the proximal hub 68.

Figure 7:
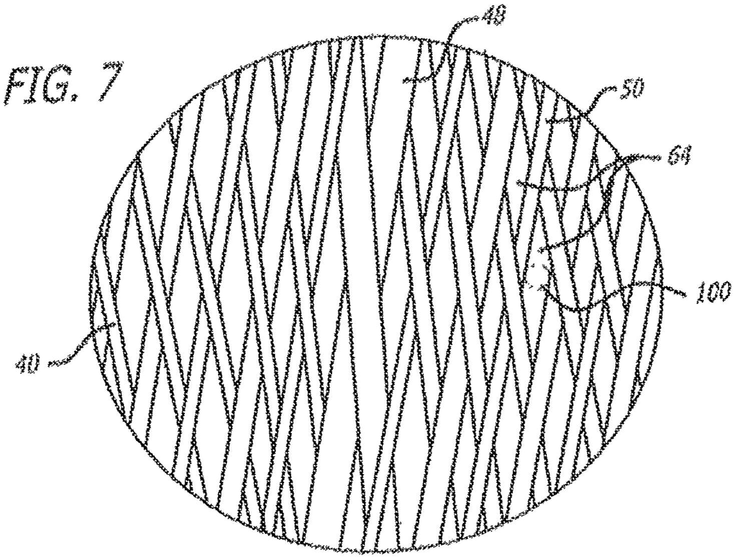
FIG. 7 is an enlarged view of the woven filament structure taken from the encircled portion 7 shown in FIG. 5.
Figure 8:
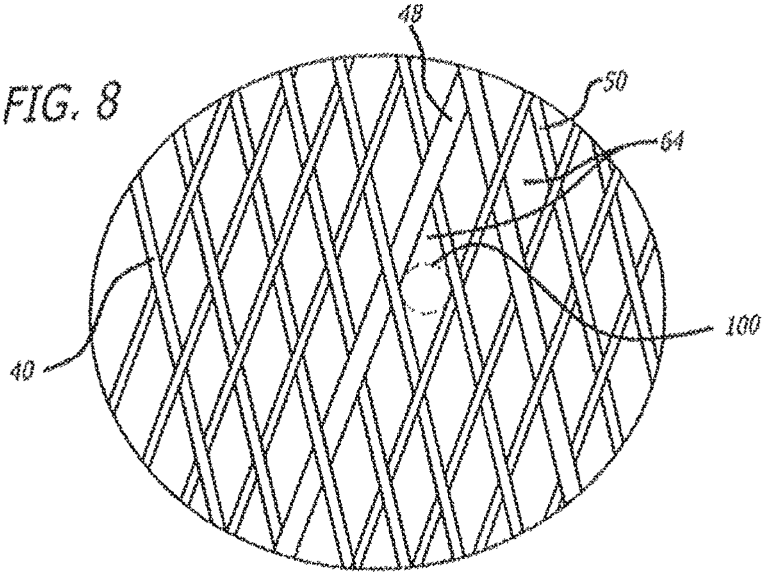
FIG. 8 is an enlarged view of the woven filament structure taken from the encircled portion 8 shown in FIG. 6.
Figure 9:
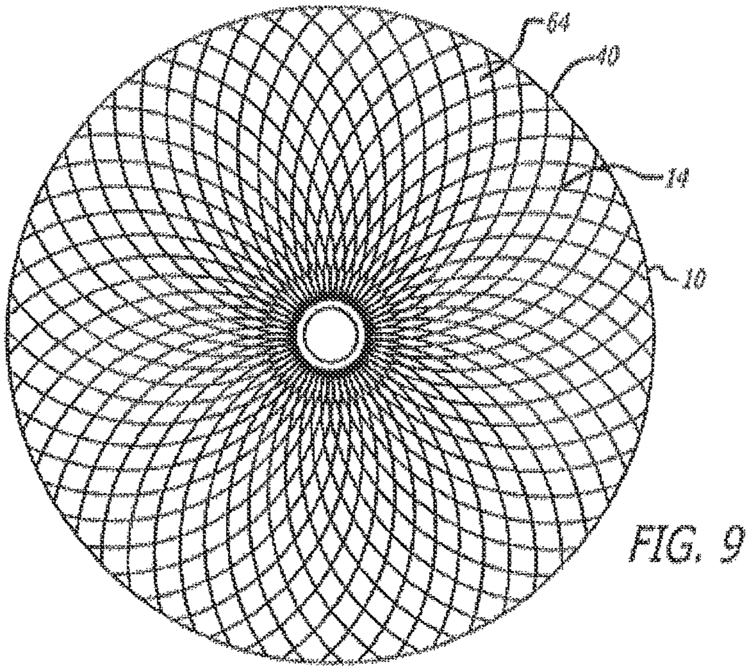
FIG. 9 is a proximal end view of the device of FIG. 3.

FIGS. 7 and 8 illustrate some configuration embodiments of braided filaments 14 of a permeable shell 40 of the device 10 for treatment of a patient's vasculature. The braid structure in each embodiment is shown with a circular shape 100 disposed within a pore 64 of a woven or braided structure with the circular shape 100 making contact with each adjacent filament segment. The pore opening size may be determined at least in part by the size of the filament elements 14 of the braid, the angle overlapping filaments make relative to each other and the picks per inch of the braid structure. For some embodiments, the cells or openings 64 may have an elongated substantially diamond shape as shown in FIG. 7, and the pores or openings 64 of the permeable shell 40 may have a substantially more square shape toward a middle portion 30 of the device 10, as shown in FIG. 8. The diamond shaped pores or openings 64 may have a length substantially greater than the width particularly near the hubs 66 and 68. In some embodiments, the ratio of diamond shaped pore or opening length to width may exceed a ratio of 3 to 1 for some cells. The diamond-shaped openings 64 may have lengths greater than the width thus having an aspect ratio, defined as Length/Width of greater than 1. The openings 64 near the hubs 66 and 68 may have substantially larger aspect ratios than those farther from the hubs as shown in FIG. 7. The aspect ratio of openings 64 adjacent the hubs may be greater than about 4 to 1. The aspect ratio of openings 64 near the largest diameter may be between about 0.75 to 1 and about 2 to 1 for some embodiments. For some embodiments, the aspect ratio of the openings 64 in the permeable shell 40 may be about 0.5 to 1 to about 2 to 1.

The pore size defined by the largest circular shapes 100 that may be disposed within openings 64 of the braided structure of the permeable shell 40 without displacing or distorting the filaments 14 surrounding the opening 64 may range in size from about 0.005 inches to about 0.01 inches, more specifically, about 0.006 inches to about 0.009 inches, even more specifically, about 0.007 inches to about 0.008 inches for some embodiments. In addition, at least some of the openings 64 formed between adjacent filaments 14 of the permeable shell 40 of the device 10 may be configured to allow blood flow through the openings 64 only at a velocity below a thrombotic threshold velocity. For some embodiments, the largest openings 64 in the permeable shell structure 40 may be configured to allow blood flow through the openings 64 only at a velocity below a thrombotic threshold velocity. As discussed above, the pore size may be less than about 0.016 inches, more specifically, less than about 0.012 inches for some embodiments. For some embodiments, the openings 64 formed between adjacent filaments 14 may be about 0.005 inches to about 0.04 inches.

Figure 12:
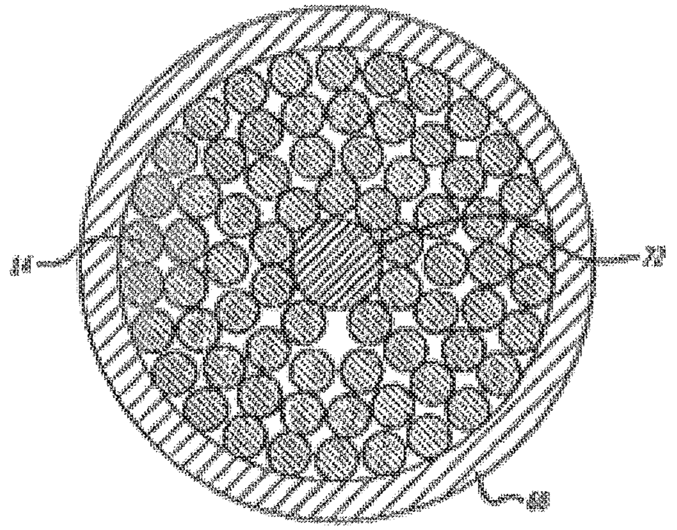
FIG. 12 illustrates an embodiment of a filament configuration for a device for treatment of a patient's vasculature.

FIG. 12 illustrates in transverse cross section an embodiment of a proximal hub 68 showing the configuration of filaments which may be tightly packed and radially constrained by an inside surface of the proximal hub 68. In some embodiments, the braided or woven structure of the permeable shell 40 formed from such filaments 14 may be constructed using a large number of small filaments. The number of filaments 14 may be greater than 125 and may also be between about 80 filaments and about 180 filaments. As discussed above, the total number of filaments 14 for some embodiments may be about 70 filaments to about 300 filaments, more specifically, about 100 filaments to about 200 filaments. In some embodiments, the braided structure of the permeable shell 40 may be constructed with two or more sizes of filaments 14. For example, the structure may have several larger filaments that provide structural support and several smaller filaments that provide the desired pore size and density and thus flow resistance to achieve a thrombotic threshold velocity in some cases. For some embodiments, small filaments 50 of the permeable shell 40 may have a transverse dimension or diameter of about 0.0006 inches to about 0.002 inches for some embodiments and about 0.0004 inches to about 0.001 inches in other embodiments. The large filaments 48 may have a transverse dimension or diameter of about 0.0015 inches to about 0.004 inches in some embodiments and about 0.001 inches to about 0.004 inches in other embodiments. The filaments 14 may be braided in a plain weave that is one under, one over structure (shown in FIGS. 7 and 8) or a supplementary weave; more than one warp interlace with one or more than one weft. The pick count may be varied between about 25 and 200 picks per inch (PPI).

The following embodiments utilize a secondary structure along an intrasaccular device to provide some benefits—such as increased flow-disruption and/or occlusion along a proximal region of the device, and increased anchoring strength along a proximal region of the device. In some embodiments, increased proximal anchoring strength may provide additional benefits, such as allowing for a softer distal portion that can better conform to the shape of the treatment site.

Figure 13:
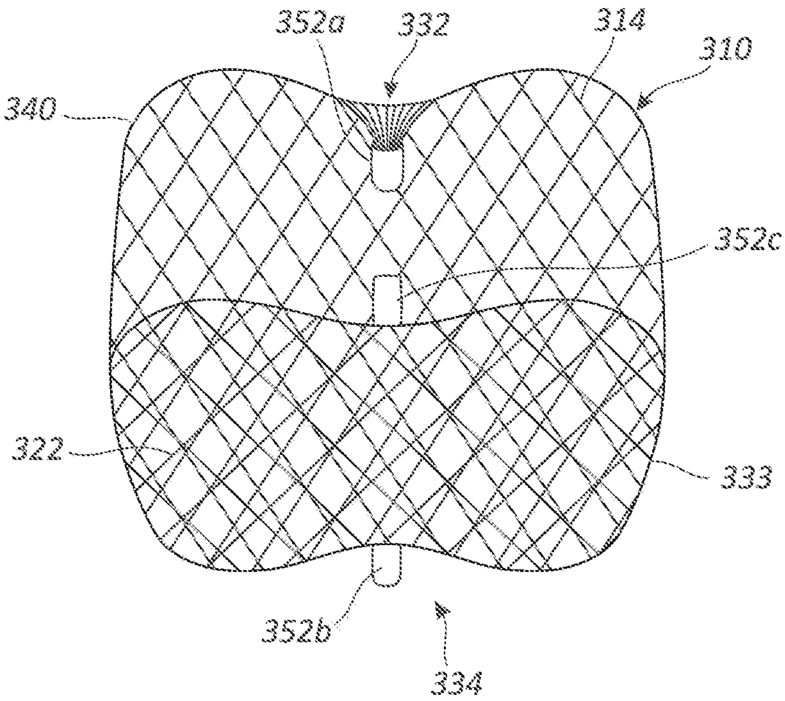
FIG. 13 illustrates a device for treatment of a patient's vasculature that includes an inverted distal end and multiple permeable shells.
Figure 14:
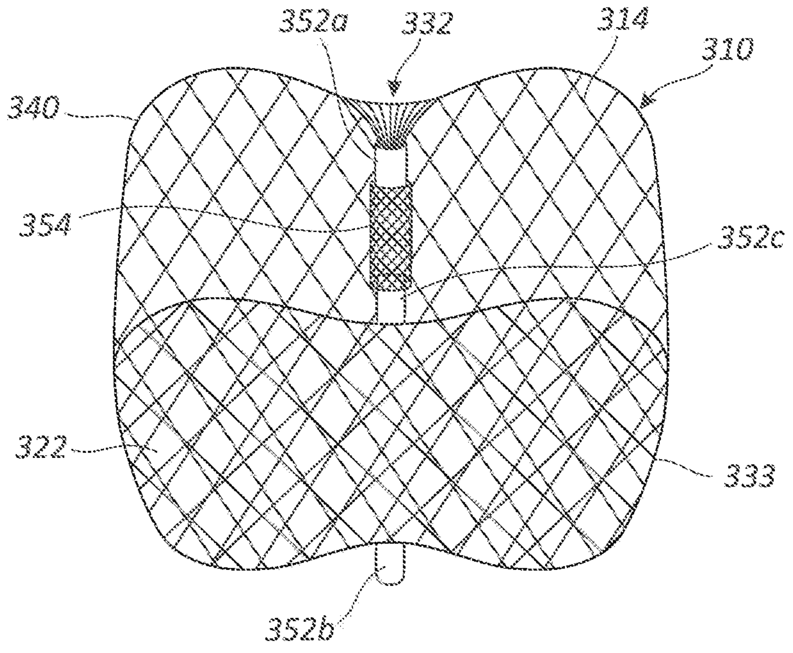
FIG. 14 illustrates an alternative device for treatment of a patient's vasculature that includes an inverted distal end and multiple permeable shells.
Figure 15A:
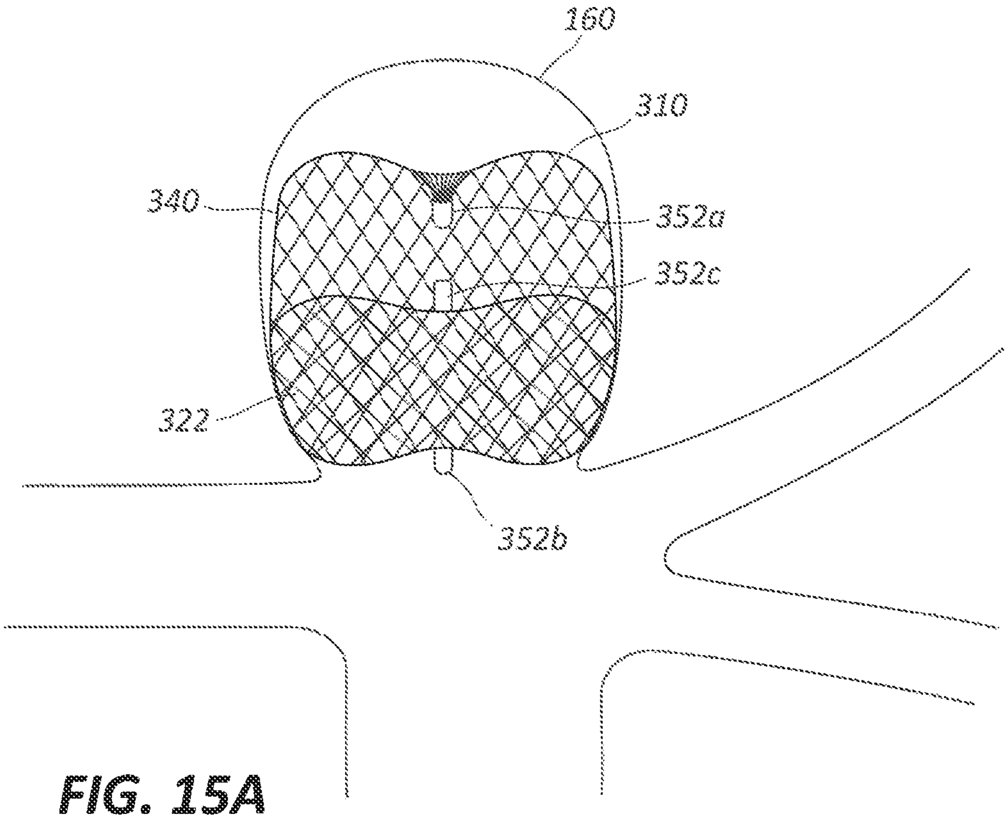
FIGS. 15A-15B illustrate the devices of FIGS. 13-14 deployed in a patient's vasculature.
Figure 15B:
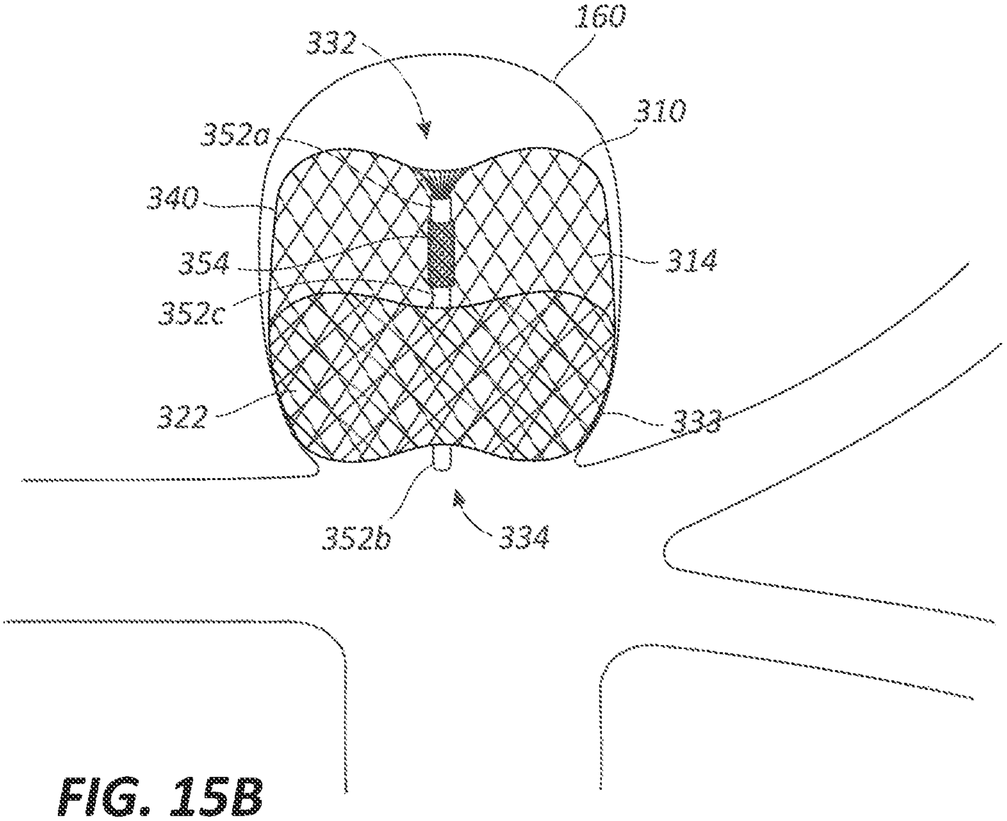

FIGS. 13-14 illustrate intrasaccular devices 310 useful for occlusion, and with particular utility to treat aneurysms. FIGS. 15A-15B depict the devices of FIGS. 13-14 deployed within an aneurysm 160. The intrasaccular devices 310 comprise a mesh of one or more braided wires or filaments 314, braided together to form the intrasaccular device 310 shape. Binding the ends of the wires 314 that form the mesh in an effective manner to keep them from separating is sometimes problematic. In the context of FIG. 13-14, the proximal and distal ends of the filaments forming the meshes are gathered or bound by a pair of tubular bands 352 at the proximal 334 and/or distal 332 ends of the devices. The proximal ends of the wires are bound to the inner or outer surface of the proximal tubular band 352*b*, while the distal ends of the wires are bound to the inner or outer surface of the distal tubular band 352*a*. This binding technique can be accomplished in a variety of ways, including welding, adhesive, and/or ties. The tubular bands 352, in one embodiment, may include a radiopaque substance such as tantalum, platinum, palladium, or gold, such that they can be used as markers used to locate the position of the intrasaccular device, particularly by helping to locate and visualize the proximal 334 and distal 332 ends of device 310.

The distal attachment point represented by the distal hub or marker band 352*a* is important because the distal portion of the intrasaccular device 310 sits within the aneurysm, toward the "top" or dome of the aneurysm. Any projecting structure can potentially contact the dome of the aneurysm and lead to complications, including rupture. The following embodiments address this issue by utilizing a recessed distal marker structure. In FIG. 13-14, the distal ends of the wires forming the intrasaccular device meshes are pulled proximally (or "down" within the context of the orientation of FIGS. 13-14) or inverted so that the distal ends of the wires or filaments 314 sit within the interior cavity of the device 310. The distal hub or marker band 352*a* is then attached to the distal ends of the wires or filaments 314 such that the distal hub or marker band 352*a* sits within the interior cavity of device 310, as shown in FIGS. 13-14. Forming an inverted distal end 332 avoids a distal projecting tip, and thereby creates an atraumatic distal region that can minimize damage to the aneurysm wall and at the dome. In this way, a distal cushion is created by the braided wires, and the distal hub or marker band sits proximally within this cushion. Inverting the distal marker (placing it in the interior cavity of the permeable shell) also provides for a softer distal end comprised of braided wires to promote top down healing. The distal hub or marker band thereby does not project from the device but still allows for visibility and ease of deployment. The depth at which the distal marker is inverted can vary depending on the required radial force of the braided device, as well as the optional presence of an additional mesh structure. The distal marker may be positioned about 0% to 50% of the total device height from the distal end, or distal most point of the device.

Going into further detail into FIG. 13, device 310 includes an outer shell 340 and an inner shell 322. As seen in FIG. 13, the proximal portion 333 of the device 340 includes a secondary internal mesh 322, which forms a multi-layer mesh device in only the proximal portion 333 of the device 310. This secondary mesh 322 acts as a secondary occlusive barrier layer to provide a flow-disruptive barrier for blood as it enters the aneurysm. The proximal portion 333 of the device 310 sits within the aneurysm along the neck, where flow-disruption along this neck section is highly important in order to provide a barrier for blood entering the aneurysm. The proximal ends of the filaments forming the inner shell 322 are also bound within the same proximal hub or marker band 352*b* at the proximal end 334 of the device 310 as the proximal ends of the filaments forming the outer shell 310. The distal portion of this inner shell 322 is connected to a different distal hub or marker band 352*c* that sits in the interior cavity of outer shell 340, as shown in FIG. 13. Because this secondary layer or inner shell 322 is only connected at its proximal end to outer shell 340, the distal part of the inner shell 322 can float or move to some degree, thereby contracting or lengthening based on the geometry of the malformation or aneurysm. In some cases, it may be desirable to limit the freedom of movement between the shells (e.g., in a particularly small aneurysm)—therefore, in some embodiments one or more connective structures (e.g., mechanical ties, adhesive, or welding) can be utilized between the inner shell 322 and outer shell 311 to limit the freedom of movement between the two structures.

One additional advantage to the secondary internal mesh 322 is that this mesh enhances the occlusive effect of the internal region of the device 340 because this mesh occupies additional space within the treatment site. This enhanced occlusive effect will be noticed in the proximal region where the secondary internal mesh 322 is located, thereby providing augmented occlusion at least along a proximal section of the device 340.

In some embodiments, this multiple layer approach can be adjusted so that the main outer structure comprises one or more layers, and the additional inner secondary structure comprises one or more additional layers. Additional layers will provide more flow-disruptive barriers and lower porosity to further reduce blood flow into the aneurysm or treatment site. The additional layers can also work to augment the occlusive effects of the device, as described above. Much of the potential for additional occlusive layers will be based on the location of the malformation and the relative size, along with the size of the vessel and the associated delivery catheter that will fit the respective vessel. Increasing the amount of overlapped wires, however, makes pushability and deliverability more difficult and increases stiffness. Thus, utilizing more than a two-layer approach may only be feasible for treatment along larger vessels, such as those not in the neurological space. For the neurological space, such as treatment of neurovascular aneurysms or to promote vessel occlusion within neurovascular blood vessels, utilizing one outer layer and one inner layer may be sufficient to occlude blood flow while still providing a deliverable device.

In a dual layer system, the one layer or shell would provide more structural integrity and the radial force required to anchor the device and oppose the walls of the aneurysm while the other layer or shell could function more as a stasis or flow-disruptive layer, providing a smaller pore size for blood and flow stasis. Either the outer 340 or the inner 322 layer could be configured as the structural layer or the stasis layer. Therefore, in one embodiment, the outer layer 340 (e.g., the layer spanning the length of the device 310) functions as the more resilient structural layer while the inner layer 322 (e.g., the inner layer spanning the proximal section of the device) functions as the stasis layer. In another embodiment, the outer layer 340 functions as the stasis layer while the inner layer 322 functions as the more resilient structural layer.

The structural layer may be comprised of about 4-48 wires, alternatively about 8-48 wires, alternatively about 4-44 wires, alternatively about 4-36 wires. The wires in the structural layer may have a diameter of about 0.001" to about 0.004", alternatively about 0.001" to about 0.003", alternatively about 0.001" to about 0.002". The structural layer may have a radial stiffness or a normalized radial stiffness between about 0.005 N/mm and 0.040 N/mm, alternatively between about 0.005 N/mm and 0.025 N/mm, alternatively between about 0.005 N/mm and 0.025 N/mm.

The stasis layer may be comprised of about 36-360 wires, alternatively about 72-216, alternatively about 96-144. The wires in the stasis layer may have a diameter of about 0.0003" to about 0.00125", alternatively about 0.0005" to about 0.001", alternatively about 0.0006" to about 0.0009". The stasis layer may have a radial stiffness or a normalized radial stiffness between about 0.001 N/mm and 0.020 N/mm, alternatively between about 0.001 N/mm and 0.010 N/mm, alternatively between about 0.001 N/mm and 0.005 N/mm.

Figure 2:
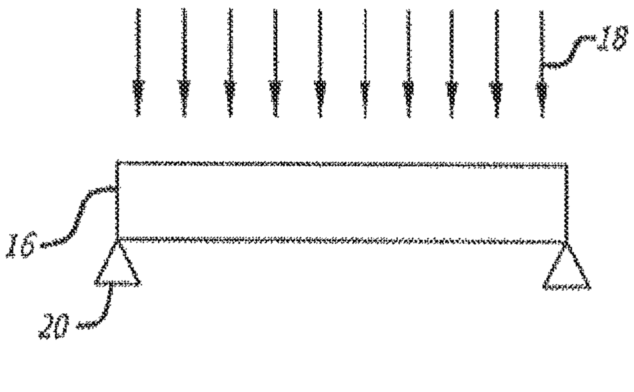
FIG. 2 is an elevation view of a beam supported by two simple supports and a plurality of arrows indicating force against the beam.
Figure 3:
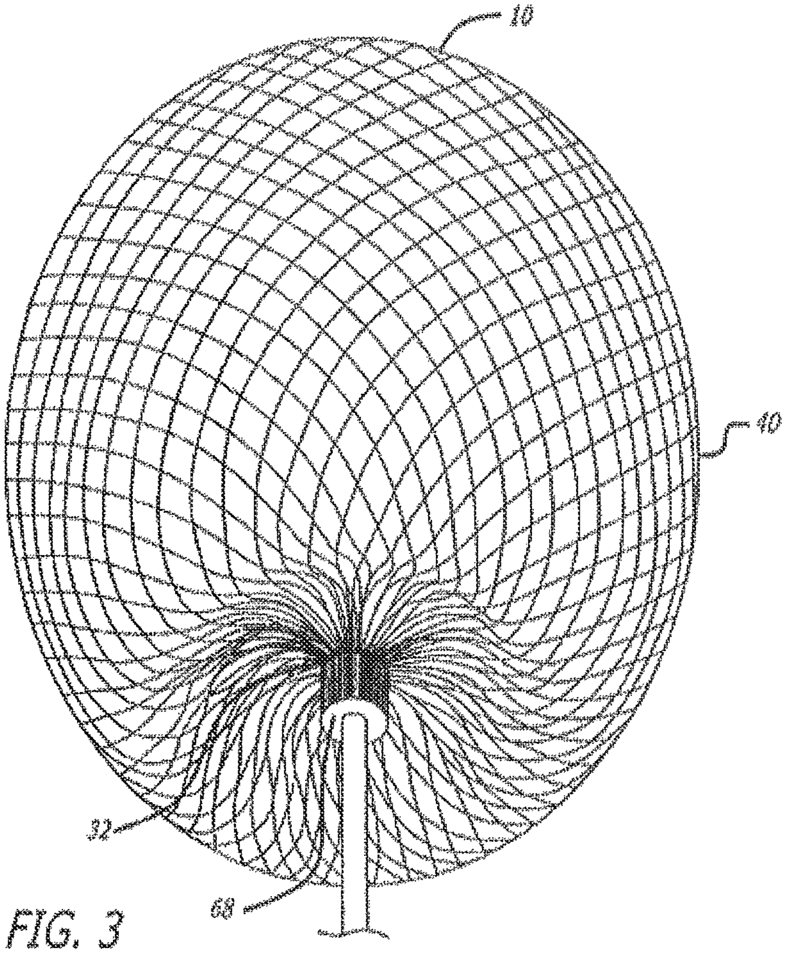
FIG. 3 is a bottom perspective view of an embodiment of a device for treatment of a patient's vasculature.

FIG. 1 depicts alternative embodiment of FIG. 13 that includes a coupler or connection mechanism 354 that connects the distal hub or marker band 352*c* of the second shell 322 to the distal hub or marker band 352*a* of the first shell 340. In various embodiments, the coupler or connection mechanism 354 may comprise one or more tethers, wires, meshes, or tubes. The connection mechanism 354 helps ensure the hubs or marker bands 352*a* and 352*c* are correctly aligned with each other so as to prevent the device 310 from being offset in a particular direction after deployment. The floating functionality of the secondary inner layer 322 of the FIG. 13 embodiment was described earlier. The connection mechanism 354 further helps control this floating functionality because the position of the distal hub or marker band 352*a* will help control how much the distal hub or marker band 352*c* floats or adjusts, because the two are connected. For instance, if the distal portion 332 of the device 310 hits the dome of an aneurysm and is relatively oversized relative to the aneurysm, the distal hub or marker band 352*a* will likely push inwards/proximally to a greater degree. This will exert force on the connection mechanism 354, in turn exerting force on the connected marker 352*c* and internal proximal mesh 322, thereby directly affecting a position of this secondary mesh 322. The connection mechanism 354 can be connected to the hubs or marker bands in various different ways, including welding, adhesive, or mechanical ties.

Figure 16A:
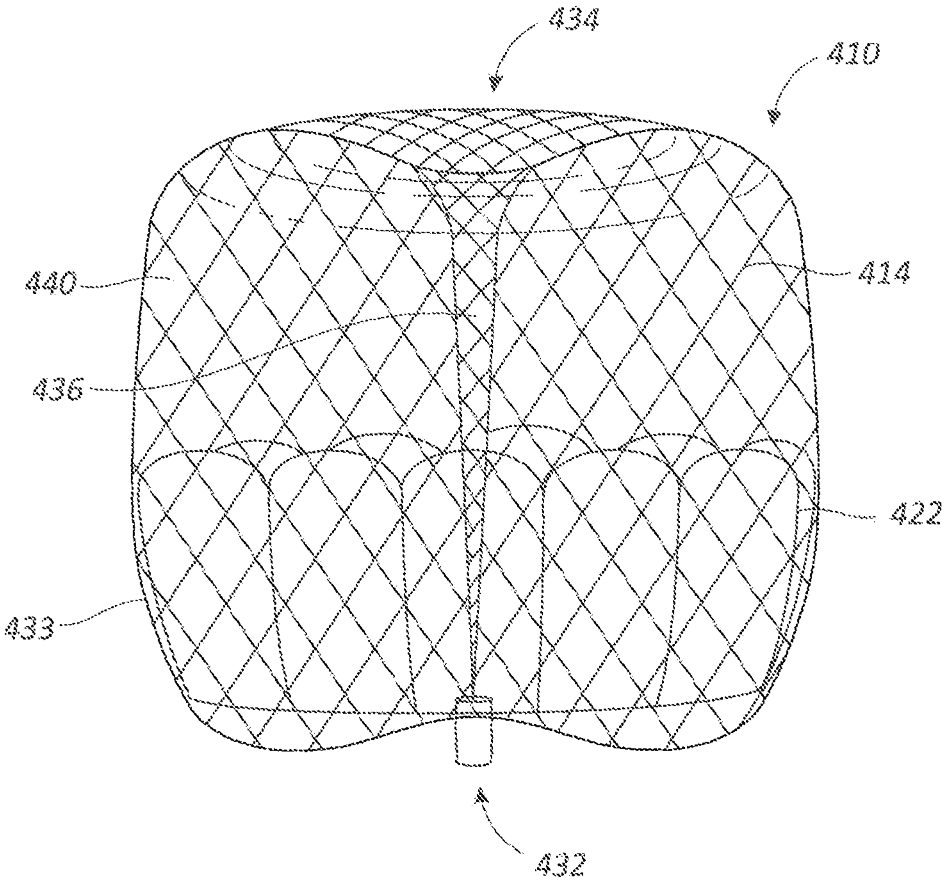
FIG. 16A illustrates an alternative device for treatment of a patient's vasculature that includes an inverted distal end and a scaffolding structure.
Figure 16B:
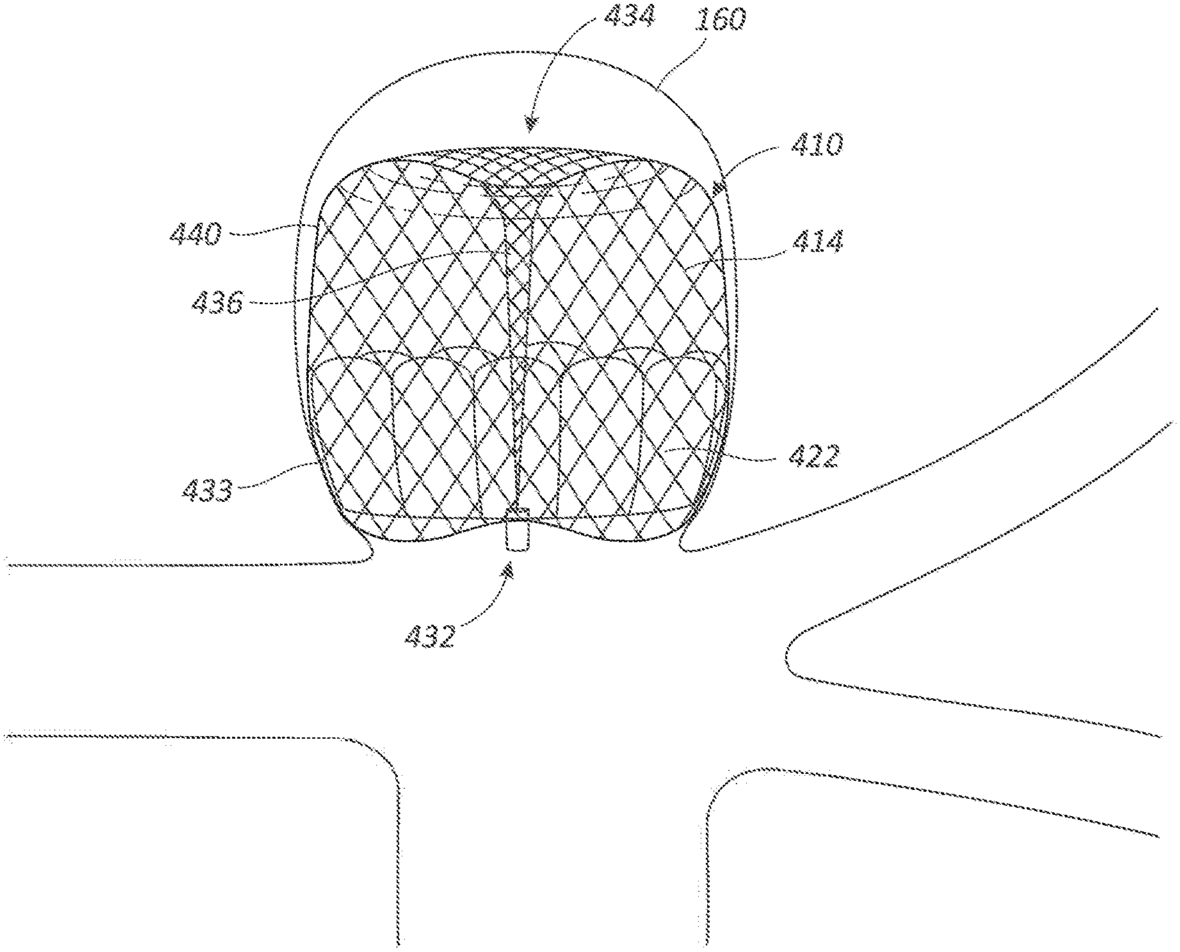
FIG. 16B illustrates the device of FIG. 16A deployed in a patient's vasculature.

FIG. 16A depicts an alternative embodiment of a mesh occlusive intrasaccular device 410. FIG. 16B depicts the embodiment of FIG. 16A deployed within an aneurysm. The proximal section 433 of the device 410 utilizes a number of scaffolding wires 422 that are preferably larger in diameter than the wires or filaments comprising the rest of the mesh 440. These scaffolding wires 422 can be placed within the mesh 440 and around the internal periphery of the mesh 440. In one embodiment, the scaffolding wires are not connected to the mesh 440. Alternatively, the scaffolding wires 422 can be coupled to the mesh 440 using welding, adhesive, or mechanical ties. Because these scaffolding wires 422 are only located in the proximal portion 433 of the device 410, they help provide a strong proximal anchor to keep the device 410 rooted to the neck of the aneurysm while also providing a flow-disruptive barrier for blood as it enters.

In addition to the scaffolding structure, this embodiment also foregoes the distal hub or marker band attachment concept for the distal ends of the wires of the mesh (as described in the other embodiments above). Instead, the distal ends of the wires or filaments 414 of the mesh occlusive device are pulled proximally back to the proximal end of the device and welded or otherwise attached to the single proximal hub or marker band, thereby creating a middle inverting layer section 436. Thus, the proximal and distal ends of the wires or filaments that are woven together to form permeable shell 440 are both gathered and secured at the proximal end 432 of the device 410. Because the distal ends of the filaments 414 are pulled through the interior cavity of permeable shell 440 and connected at the proximal end of the device 410, no distal wire attachment structure or hub is needed. In this way, the issue with a distal projecting structure that can otherwise contact the dome of the aneurysm is avoided entirely.

The inclusion of middle inverting layer 436 may offer additional advantages, for instance less connection points by having just one common proximal marker connection junction for the various sires comprising the device 410. Furthermore, the mesh layer comprising the length of device 410 can utilize relatively softer wires to promote conformability due to the anchoring force provided by scaffolding wires 422, which can allow device 410 to have some degree of conformability to adopt to the shape of the treatment region.

Alternative embodiments can utilize the scaffolding structure along with the distal hub or marker band configuration of other embodiments. In other words, the scaffolding structure can be further included on other embodiments described earlier in order to augment the proximal retention force of other instrasaccular device embodiments presented so far.

The permeable mesh shell 440 may be comprised of about 4-48 wires, alternatively about 8-48 wires, alternatively about 4-44 wires, alternatively about 4-36 wires. The wires in the structural layer may have a diameter of about 0.0003" to about 0.00125", alternatively about 0.0005" to about 0.001", alternatively about 0.0006" to about 0.0009". The permeable shell may also have filaments made with different materials. For instance, the permeable shell may contain filaments made from nitinol and also contain composite (DFT) filaments. The permeable shell 440 may have a radial stiffness or a normalized radial stiffness between about 0.001 N/mm and 0.020 N/mm, alternatively between about 0.001 N/mm and 0.010 N/mm, alternatively between about 0.001 N/mm and 0.005 N/mm.

The scaffolding structure may include about 4 to about 48 wires, alternatively about 8 to about 48 wires, alternatively about 4 to about 44 wires, alternatively about 4 to about 36 wires. The scaffolding wires may have a diameter of about 0.001" to about 0.004", alternatively about 0.001" to about 0.003", alternatively about 0.001" to about 0.002". The scaffolding wires may have a diameter between about 233.33 and about 220%, alternatively between about 100 and about 200%, alternatively between about 66.67 and about 122% bigger than the diameter of the wires forming the permeable mesh shell 440. The scaffolding wires 422 may be made from nitinol, stainless steel, radiopaque material (e.g., tantalum, platinum, palladium, or gold) or DFT utilizing a radiopaque core and a nitinol outer jacket. The scaffolding structure may have a radial stiffness or a normalized radial stiffness between about 0.005 N/mm and 0.040 N/mm, alternatively between about 0.005 N/mm and 0.025 N/mm, alternatively between about 0.005 N/mm and 0.020 N/mm.

The expanded state of the scaffolding structure may have a scalloped shaped open distal end wherein the scaffolding wires or filaments extend distally from a proximal end and curve back in a proximal direction to form a curved shape in a distal region. Adjacent scaffolding filaments may be connected together to form the scalloped shape open distal end.

The scaffolding structure may be located in the proximal portion of the device 410. The proximal section 433 of the permeable shell 410 may have a length that is about ½, alternatively about ¼, of the length of the permeable shell in its expanded state. The proximal section 433 of the permeable shell 410 may comprise the portion beginning at the proximal end 432 and extending to about 20% or less, alternatively about 25% or less, alternatively about 30% or less, alternatively about 33% or less, alternatively about 40% or less, alternatively about 50% or less of the total length of the expanded state of the device 410. The proximal section 433 of the permeable shell 410 may comprise the portion beginning at the proximal end 432 and extending to between about 10% to about 50%, alternatively between about 10% and about 40%, alternatively between about 10% and about 30%, alternatively between about 15% and about 50%, alternatively between about 15% and about 40%, alternatively between about 20% and about 40% of the total length of the expanded state of the device 410.

For some embodiments, the permeable shell 40, 340, 440 or portions thereof may be porous and may be highly permeable to liquids. In contrast to most vascular prosthesis fabrics or grafts which typically have a water permeability below 2,000 ml/min/cm$^2$ when measured at a pressure of 120 mmHg, the permeable shell 40 of some embodiments discussed herein may have a water permeability greater than about 2,000 ml/min/cm$^2$, in some cases greater than about 2,500 ml/min/cm$^2$. For some embodiments, water permeability of the permeable shell 40 or portions thereof may be between about 2,000 and 10,000 ml/min/cm$^2$, more specifically, about 2,000 ml/min/cm$^2$ to about 15,000 ml/min/cm$^2$, when measured at a pressure of 120 mmHg.

Device embodiments and components thereof may include metals, polymers, biologic materials and composites thereof. Suitable metals include zirconium-based alloys, cobalt-chrome alloys, nickel-titanium alloys, platinum, tantalum, stainless steel, titanium, gold, and tungsten. Potentially suitable polymers include but are not limited to acrylics, silk, silicones, polyvinyl alcohol, polypropylene, polyvinyl alcohol, polyesters (e.g. polyethylene terephthalate or PET), PolyEtherEther Ketone (PEEK), polytetrafluoroethylene (PTFE), polycarbonate urethane (PCU) and polyurethane (PU). Device embodiments may include a material that degrades or is absorbed or eroded by the body. A bioresorbable (e.g., breaks down and is absorbed by a cell, tissue, or other mechanism within the body) or bioabsorbable (similar to bioresorbable) material may be used. Alternatively, a bioerodable (e.g., erodes or degrades over time by contact with surrounding tissue fluids, through cellular activity or other physiological degradation mechanisms), biodegradable (e.g., degrades over time by enzymatic or hydrolytic action, or other mechanism in the body), or dissolvable material may be employed. Each of these terms is interpreted to be interchangeable. bioabsorbable polymer. Potentially suitable bioabsorbable materials include polylactic acid (PLA), poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials. An absorbable composite fiber may be made by combining a reinforcement fiber made from a copolymer of about 18% glycolic acid and about 82% lactic acid with a matrix material consisting of a blend of the above copolymer with about 20% polycaprolactone (PCL).

Permeable shell embodiments 40, 340, 440 may be formed at least in part of wire, ribbon, or other filamentary elements 14, 314, 414. These filamentary elements 14 may have circular, elliptical, ovoid, square, rectangular, or triangular cross-sections. Permeable shell embodiments 40 may also be formed using conventional machining, laser cutting, electrical discharge machining (EDM) or photochemical machining (PCM). If made of a metal, it may be formed from either metallic tubes or sheet material.

Figure 17:
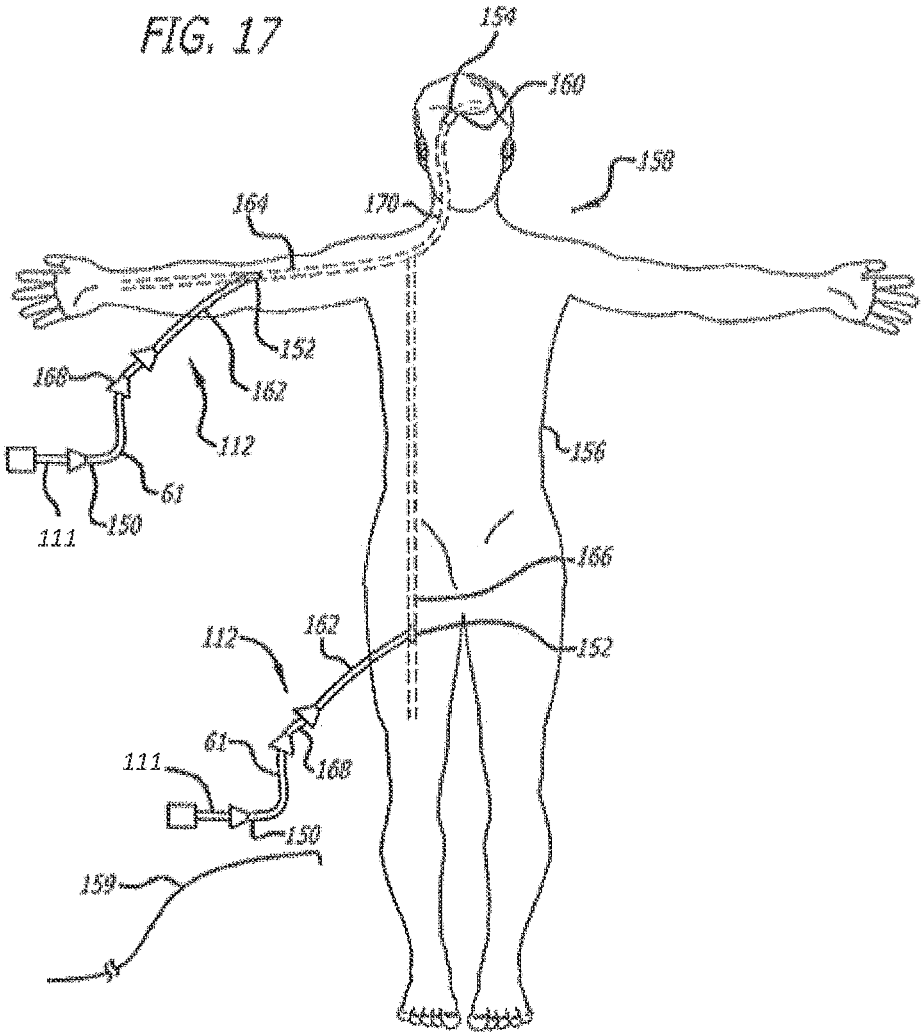
FIG. 17 is a schematic view of a patient being accessed by an introducer sheath, a microcatheter and a device for treatment of a patient's vasculature releasably secured to a distal end of a delivery device or actuator.
Figure 18:
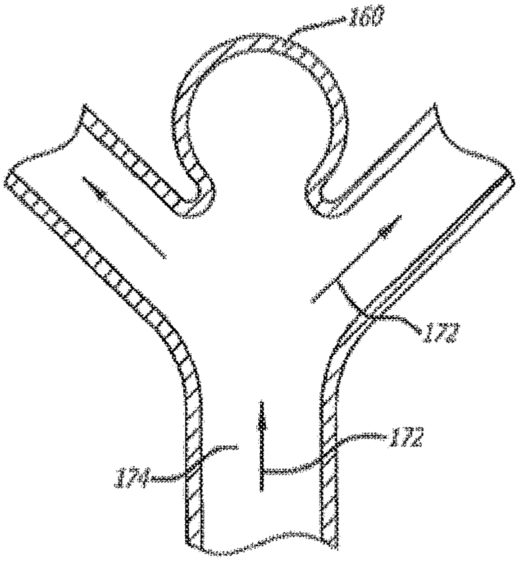
FIG. 18 is a sectional view of a terminal aneurysm.

Device embodiments 10, 310, 410 discussed herein may be delivered and deployed from a delivery and positioning system 112 that includes a microcatheter 61, such as the type of microcatheter 61 that is known in the art of neurovascular navigation and therapy. Device embodiments for treatment of a patient's vasculature 10, 310, 410 may be elastically collapsed and restrained by a tube or other radial restraint, such as an inner lumen 120 of a microcatheter 61, for delivery and deployment. The microcatheter 61 may generally be inserted through a small incision 152 accessing a peripheral blood vessel such as the femoral artery or brachial artery. The microcatheter 61 may be delivered or otherwise navigated to a desired treatment site 154 from a position outside the patient's body 156 over a guidewire 159 under fluoroscopy or by other suitable guiding methods. The guidewire 159 may be removed during such a procedure to allow insertion of the device 10, 310, 410 secured to a delivery apparatus 111 of the delivery system 112 through the inner lumen 120 of a microcatheter 61 in some cases. FIG. 17 illustrates a schematic view of a patient 158 undergoing treatment of a vascular defect 160 as shown in FIG. 18. An access sheath 162 is shown disposed within either a radial artery 164 or femoral artery 166 of the patient 158 with a delivery system 112 that includes a microcatheter 61 and delivery apparatus 111 disposed within the access sheath 162. The delivery system 112 is shown extending distally into the vasculature of the patient's brain adjacent a vascular defect 160 in the patient's brain.

Access to a variety of blood vessels of a patient may be established, including arteries such as the femoral artery 166, radial artery 164, and the like in order to achieve percutaneous access to a vascular defect 160. In general, the patient 158 may be prepared for surgery and the access artery is exposed via a small surgical incision 152 and access to the lumen is gained using the Seldinger technique where an introducing needle is used to place a wire over which a dilator or series of dilators dilates a vessel allowing an introducer sheath 162 to be inserted into the vessel. This would allow the device to be used percutaneously. With an introducer sheath 162 in place, a guiding catheter 168 is then used to provide a safe passageway from the entry site to a region near the target site 154 to be treated. For example, in treating a site in the human brain, a guiding catheter 168 would be chosen which would extend from the entry site 152 at the femoral artery up through the large arteries extending around the heart through the aortic arch, and downstream through one of the arteries extending from the upper side of the aorta such as the carotid artery 170. Typically, a guidewire 159 and neurovascular microcatheter 61 are then placed through the guiding catheter 168 and advanced through the patient's vasculature, until a distal end 151 of the microcatheter 61 is disposed adjacent or within the target vascular defect 160, such as an aneurysm. Exemplary guidewires 159 for neurovascular use include the Synchro2® made by Boston Scientific and the Glidewire Gold Neuro® made by MicroVention Terumo. Typical guidewire sizes may include 0.014 inches and 0.018 inches. Once the distal end 151 of the catheter 61 is positioned at the site, often by locating its distal end through the use of radiopaque marker material and fluoroscopy, the catheter is cleared. For example, if a guidewire 159 has been used to position the microcatheter 61, it is withdrawn from the catheter 61 and then the implant delivery apparatus 111 is advanced through the microcatheter 61.

Delivery and deployment of device embodiments 10, 310, 410 discussed herein may be carried out by first compressing the device 10, 310, 410 to a radially constrained and longitudinally flexible state as shown in FIG. 11. The device 10, 310, 410 may then be delivered to a desired treatment site 154 while disposed within the microcatheter 61, and then ejected or otherwise deployed from a distal end 151 of the microcatheter 61. In other method embodiments, the microcatheter 61 may first be navigated to a desired treatment site 154 over a guidewire 159 or by other suitable navigation techniques. The distal end of the microcatheter 61 may be positioned such that a distal port of the microcatheter 61 is directed towards or disposed within a vascular defect 160 to be treated and the guidewire 159 withdrawn. The device 10, 310, 410 secured to a suitable delivery apparatus 111 may then be radially constrained, inserted into a proximal portion of the inner lumen 120 of the microcatheter 61 and distally advanced to the vascular defect 160 through the inner lumen 120.

Once disposed within the vascular defect 160, the device 10, 310, 410 may then allowed to assume an expanded relaxed or partially relaxed state with the permeable shell 40, 340, 440 of the device spanning or partially spanning a portion of the vascular defect 160 or the entire vascular defect 160. The device 10, 310, 410 may also be activated by the application of an energy source to assume an expanded deployed configuration once ejected from the distal section of the microcatheter 61 for some embodiments. Once the device 10 is deployed at a desired treatment site 154, the microcatheter 61 may then be withdrawn.

Figure 19:
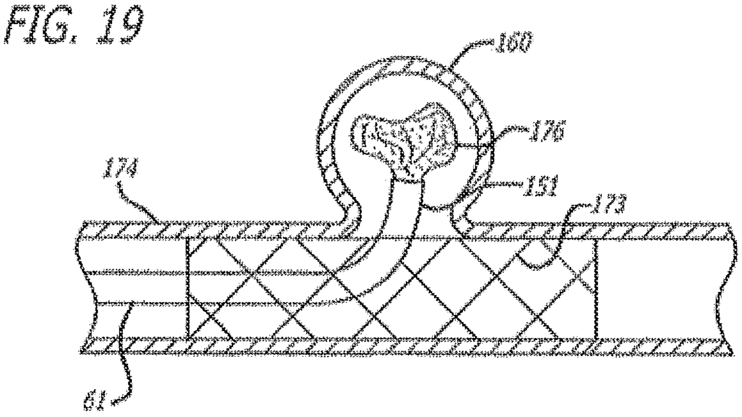
FIG. 19 is a sectional view of an aneurysm.

Some embodiments of devices for the treatment of a patient's vasculature 10, 310, 410 discussed herein may be directed to the treatment of specific types of defects of a patient's vasculature. For example, referring to FIG. 18, an aneurysm 160 commonly referred to as a terminal aneurysm is shown in section. Terminal aneurysms occur typically at bifurcations in a patient's vasculature where blood flow, indicated by the arrows 172, from a supply vessel splits into two or more branch vessels directed away from each other. The main flow of blood from the supply vessel 174, such as a basilar artery, sometimes impinges on the vessel where the vessel diverges and where the aneurysm sack forms. Terminal aneurysms may have a well defined neck structure where the profile of the aneurysm 160 narrows adjacent the nominal vessel profile, but other terminal aneurysm embodiments may have a less defined neck structure or no neck structure. FIG. 19 illustrates a typical berry type aneurysm 160 in section where a portion of a wall of a nominal vessel section weakens and expands into a sack like structure ballooning away from the nominal vessel surface and profile. Some berry type aneurysms may have a well defined neck structure as shown in FIG. 19, but others may have a less defined neck structure or none at all. FIG. 19 also shows some optional procedures wherein a stent 173 or other type of support has been deployed in the parent vessel 174 adjacent the aneurysm. Also, shown is embolic material 176 being deposited into the aneurysm 160 through a microcatheter 61. Either or both of the stent 173 and embolic material 176 may be so deployed either before or after the deployment of a device for treatment of a patient's vasculature 10.

Prior to delivery and deployment of a device for treatment of a patient's vasculature 10, 310, 410, it may be desirable for the treating physician to choose an appropriately sized device 10, 310, 410 to optimize the treatment results. Some embodiments of treatment may include estimating a volume of a vascular site or defect 160 to be treated and selecting a device 10, 310, 410 with a volume that is substantially the same volume or slightly over-sized relative to the volume of the vascular site or defect 160. The volume of the vascular defect 160 to be occluded may be determined using three-dimensional angiography or other similar imaging techniques along with software which calculates the volume of a selected region. The amount of over-sizing may be between about 2% and 15% of the measured volume. In some embodiments, such as a very irregular shaped aneurysm, it may be desirable to under-size the volume of the device 10, 310, 410. Small lobes or "daughter aneurysms" may be excluded from the volume, defining a truncated volume which may be only partially filled by the device without affecting the outcome. A device 10, 310, 410 deployed within such an irregularly shaped aneurysm 160 is shown in FIG. 28 discussed below. Such a method embodiment may also include implanting or deploying the device 10, 310, 410 so that the vascular defect 160 is substantially filled volumetrically by a combination of device and blood contained therein. The device 10, 310, 410 may be configured to be sufficiently conformal to adapt to irregular shaped vascular defects 160 so that at least about 75%, in some cases about 80%, of the vascular defect volume is occluded by a combination of device 10, 310, 410 and blood contained therein.

Figure 20:
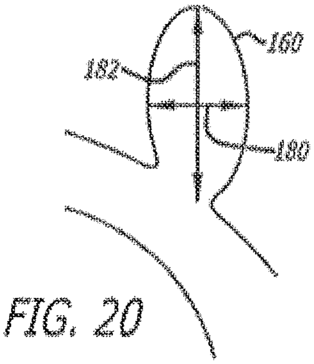
FIG. 20 is a schematic view in section of an aneurysm showing perpendicular arrows which indicate interior nominal longitudinal and transverse dimensions of the aneurysm.
Figure 21:
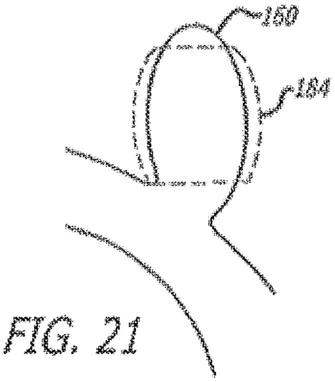
FIG. 21 is a schematic view in section of the aneurysm of FIG. 20 with a dashed outline of a device for treatment of a patient's vasculature in a relaxed unconstrained state that extends transversely outside of the walls of the aneurysm.
Figure 22:
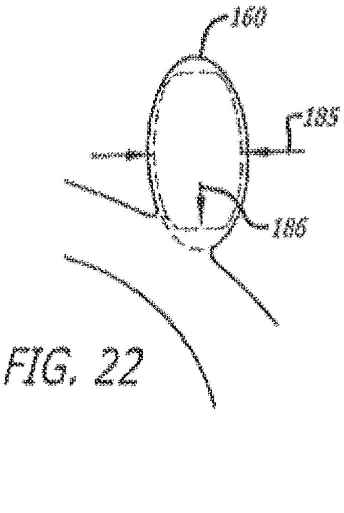
FIG. 22 is a schematic view in section of an outline of a device represented by the dashed line in FIG. 21 in a deployed and partially constrained state within the aneurysm.

In particular, for some treatment embodiments, it may be desirable to choose a device 10, 310, 410 that is properly oversized in a transverse dimension so as to achieve a desired conformance, radial force and fit after deployment of the device 10. FIGS. 20-22 illustrate a schematic representation of how a device 10, 310, 410 may be chosen for a proper fit after deployment that is initially oversized in a transverse dimension by at least about 10% of the largest transverse dimension of the vascular defect 160 and sometimes up to about 100% of the largest transverse dimension. For some embodiments, the device 10, 310, 410 may be oversized a small amount (e.g. less than about 1.5 mm) in relation to measured dimensions for the width, height or neck diameter of the vascular defect 160.

In FIG. 20, a vascular defect 160 in the form of a cerebral aneurysm is shown with horizontal arrows 180 and vertical arrows 182 indicating the approximate largest interior dimensions of the defect 160. Arrow 180 extending horizontally indicates the largest transverse dimension of the defect 160. In FIG. 21, a dashed outline 184 of a device for treatment of the vascular defect is shown superimposed over the vascular defect 160 of FIG. 20 illustrating how a device 10, 310, 410 that has been chosen to be approximately 20% oversized in a transverse dimension would look in its unconstrained, relaxed state. FIG. 22 illustrates how the device 10, 310, 410, which is indicated by the dashed line 184 of FIG. 21 might conform to the interior surface of the vascular defect 160 after deployment whereby the nominal transverse dimension of the device 10, 310, 410 in a relaxed unconstrained state has now been slightly constrained by the inward radial force 185 exerted by the vascular defect 160 on the device 10, 310, 410. In response, as the filaments 14, 314, 414 of the device 10, 310, 410 and thus the permeable shell 40, 340, 440 made therefrom have a constant length, the device 10, 310, 410 has assumed a slightly elongated shape in the axial or longitudinal axis of the device 10 so as to elongate and better fill the interior volume of the defect 160 as indicated by the downward arrow 186 in FIG. 22.

Once a properly sized device 10, 310, 410 has been selected, the delivery and deployment process may then proceed. It should also be noted also that the properties of the device embodiments 10, 310, 410 and delivery system embodiments 112 discussed herein generally allow for retraction of a device 10 after initial deployment into a defect 160, but before detachment of the device 10, 310, 410. Therefore, it may also be possible and desirable to withdraw or retrieve an initially deployed device 10 after the fit within the defect 160 has been evaluated in favor of a differently sized device 10, 310, 410. An example of a terminal aneurysm 160 is shown in FIG. 23 in section. The tip 151 of a catheter, such as a microcatheter 61 may be advanced into or adjacent the vascular site or defect 160 (e.g. aneurysm) as shown in FIG. 24. For some embodiments, an embolic coil or other vaso-occlusive device or material 176 (as shown for example in FIG. 19) may optionally be placed within the aneurysm 160 to provide a framework for receiving the device 10, 310, 410. In addition, a stent 173 may be placed within a parent vessel 174 of some aneurysms substantially crossing the aneurysm neck prior to or during delivery of devices for treatment of a patient's vasculature discussed herein (also as shown for example in FIG. 19). An example of a suitable microcatheter 61 having an inner lumen diameter of about 0.020 inches to about 0.022 inches is the Rapid Transit® manufactured by Cordis Corporation. Examples of some suitable microcatheters 61 may include microcatheters having an inner lumen diameter of about 0.026 inch to about 0.028 inch, such as the Rebar® by Ev3 Company, the Renegade Hi-Flow® by Boston Scientific Corporation, and the Mass Transit® by Cordis Corporation. Suitable microcatheters having an inner lumen diameter of about 0.031 inch to about 0.033 inch may include the Marksmen® by Chestnut Medical Technologies, Inc. and the Vasco 28® by Balt Extrusion. A suitable microcatheter 61 having an inner lumen diameter of about 0.039 inch to about 0.041 inch includes the Vasco 35 by Balt Extrusion. These microcatheters 61 are listed as exemplary embodiments only, other suitable microcatheters may also be used with any of the embodiments discussed herein.

Detachment of the device 10, 310, 410 from the delivery apparatus 111 may be controlled by a control switch 188 disposed at a proximal end of the delivery system 112, which may also be coupled to an energy source 142, which severs the tether 72 that secures the proximal hub 68 of the device 10 to the delivery apparatus 111. While disposed within the microcatheter 61 or other suitable delivery system 112, as shown in FIG. 11, the filaments 14, 314, 414 of the permeable shell 40, 340, 440 may take on an elongated, non-everted configuration substantially parallel to each other and a longitudinal axis of the catheter 61. Once the device 10, 310, 410 is pushed out of the distal port of the microcatheter 61, or the radial constraint is otherwise removed, the distal ends 62 of the filaments 14, 314, 414 may then axially contract towards each other so as to assume the globular everted configuration within the vascular defect 160 as shown in FIG. 25.

The device 10, 310, 410 may be inserted through the microcatheter 61 such that the catheter lumen 120 restrains radial expansion of the device 10, 310, 410 during delivery. Once the distal tip or deployment port of the delivery system 112 is positioned in a desirable location adjacent or within a vascular defect 160, the device 10, 310, 410 may be deployed out the distal end of the catheter 61 thus allowing the device to begin to radially expand as shown in FIG. 25. As the device 10, 310, 410 emerges from the distal end of the delivery system 112, the device 10, 310, 410 expands to an expanded state within the vascular defect 160, but may be at least partially constrained by an interior surface of the vascular defect 160.

Upon full deployment, radial expansion of the device 10, 310, 410 may serve to secure the device 10, 310, 410 within the vascular defect 160 and also deploy the permeable shell 40 across at least a portion of an opening 190 (e.g. aneurysm neck) so as to at least partially isolate the vascular defect 160 from flow, pressure or both of the patient's vasculature adjacent the vascular defect 160 as shown in FIG. 26. The conformability of the device 10, 310, 410, particularly in the neck region 190 may provide for improved sealing. For some embodiments, once deployed, the permeable shell 40, 340, 440 may substantially slow the flow of fluids and impede flow into the vascular site and thus reduce pressure within the vascular defect 160. For some embodiments, the device 10, 310, 410 may be implanted substantially within the vascular defect 160, however, in some embodiments, a portion of the device 10, 310, 410 may extend into the defect opening or neck 190 or into branch vessels.

For some embodiments, as discussed above, the device 10, 310, 410 may be manipulated by the user to position the device 10, 310, 410 within the vascular site or defect 160 during or after deployment but prior to detachment. For some embodiments, the device 10, 310, 410 may be rotated in order to achieve a desired position of the device 10 and, more specifically, a desired position of the permeable shell 40, 340, 440, prior to or during deployment of the device 10, 310, 410. For some embodiments, the device 10, 310, 410 may be rotated about a longitudinal axis of the delivery system 112 with or without the transmission or manifestation of torque being exhibited along a middle portion of a delivery catheter being used for the delivery. It may be desirable in some circumstances to determine whether acute occlusion of the vascular defect 160 has occurred prior to detachment of the device 10, 310, 410 from the delivery apparatus 111 of the delivery system 112. These delivery and deployment methods may be used for deployment within berry aneurysms, terminal aneurysms, or any other suitable vascular defect embodiments 160. Some method embodiments include deploying the device 10, 310, 410 at a confluence of three vessels of the patient's vasculature that form a bifurcation such that the permeable shell 40 of the device 10, 310, 410 substantially covers the neck of a terminal aneurysm. Once the physician is satisfied with the deployment, size and position of the device 10, 310, 410, the device 10, 310, 410 may then be detached by actuation of the control switch 188 by the methods described above and shown in FIG. 26. Thereafter, the device 10, 310, 410 is in an implanted state within the vascular defect 160 to effect treatment thereof.

FIG. 27 illustrates another configuration of a deployed and implanted device in a patient's vascular defect 160. While the implantation configuration shown in FIG. 26 indicates a configuration whereby the longitudinal axis 46 of the device 10, 310, 410 is substantially aligned with a longitudinal axis of the defect 160, other suitable and clinically effective implantation embodiments may be used. For example, FIG. 27 shows an implantation embodiment whereby the longitudinal axis 46 of the implanted device 10, 310, 410 is canted at an angle of about 10 degrees to about 90 degrees relative to a longitudinal axis of the target vascular defect 160. Such an alternative implantation configuration may also be useful in achieving a desired clinical outcome with acute occlusion of the vascular defect 160 in some cases and restoration of normal blood flow adjacent the treated vascular defect. FIG. 28 illustrates a device 10, 310, 410 implanted in an irregularly shaped vascular defect 160. The aneurysm 160 shown has at least two distinct lobes 192 extending from the main aneurysm cavity. The two lobes 192 shown are unfilled by the deployed vascular device 10, 310, 410, yet the lobes 192 are still isolated from the parent vessel of the patient's body due to the occlusion of the aneurysm neck portion 190. Markers, such as radiopaque markers, on the device 10, 310, 410 or delivery system 112 may be used in conjunction with external imaging equipment (e.g. x-ray) to facilitate positioning of the device or delivery system during deployment. Once the device is properly positioned, the device 10 may be detached by the user. For some embodiments, the detachment of the device 10, 310, 410 from the delivery apparatus 111 of the delivery system 112 may be affected by the delivery of energy (e.g. heat, radiofrequency, ultrasound, vibrational, or laser) to a junction or release mechanism between the device 10 and the delivery apparatus 111. Once the device 10, 310, 410 has been detached, the delivery system 112 may be withdrawn from the patient's vasculature or patient's body 158. For some embodiments, a stent 173 may be place within the parent vessel substantially crossing the aneurysm neck 190 after delivery of the device 10 as shown in FIG. 19 for illustration.

For some embodiments, a biologically active agent or a passive therapeutic agent may be released from a responsive material component of the device 10, 310, 410. The agent release may be affected by one or more of the body's environmental parameters or energy may be delivered (from an internal or external source) to the device 10, 310, 410. Hemostasis may occur within the vascular defect 160 as a result of the isolation of the vascular defect 160, ultimately leading to clotting and substantial occlusion of the vascular defect 160 by a combination of thrombotic material and the device 10, 310, 410. For some embodiments, thrombosis within the vascular defect 160 may be facilitated by agents released from the device 10 and/or drugs or other therapeutic agents delivered to the patient.

For some embodiments, once the device 10, 310, 410 has been deployed, the attachment of platelets to the permeable shell 40 may be inhibited and the formation of clot within an interior space of the vascular defect 160, device, or both promoted or otherwise facilitated with a suitable choice of thrombogenic coatings, anti-thrombogenic coatings or any other suitable coatings (not shown) which may be disposed on any portion of the device 10, 310, 410 for some embodiments, including an outer surface of the filaments 14 or the hubs 66 and 68. Such a coating or coatings may be applied to any suitable portion of the permeable shell 40. Energy forms may also be applied through the delivery apparatus 111 and/or a separate catheter to facilitate fixation and/or healing of the device 10, 310, 410 adjacent the vascular defect 160 for some embodiments. One or more embolic devices or embolic material 176 may also optionally be delivered into the vascular defect 160 adjacent permeable shell portion that spans the neck or opening 190 of the vascular defect 160 after the device 10 has been deployed. For some embodiments, a stent or stent-like support device 173 may be implanted or deployed in a parent vessel adjacent the defect 160 such that it spans across the vascular defect 160 prior to or after deployment of the vascular defect treatment device 10, 310, 410.

In any of the above embodiments, the device 10, 310, 410 may have sufficient radial compliance so as to be readily retrievable or retractable into a typical microcatheter 61. The proximal portion of the device 10, 310, 410, or the device as a whole for some embodiments, may be engineered or modified by the use of reduced diameter filaments, tapered filaments, or filaments oriented for radial flexure so that the device 10, 310, 410 is retractable into a tube that has an internal diameter that is less than about 0.7 mm, using a retraction force less than about 2.7 Newtons (0.6 lbf) force. The force for retrieving the device 10, 310, 410 into a microcatheter 61 may be between about 0.8 Newtons (0.18 lbf) and about 2.25 Newtons (0.5 lbf).

Figure 29:
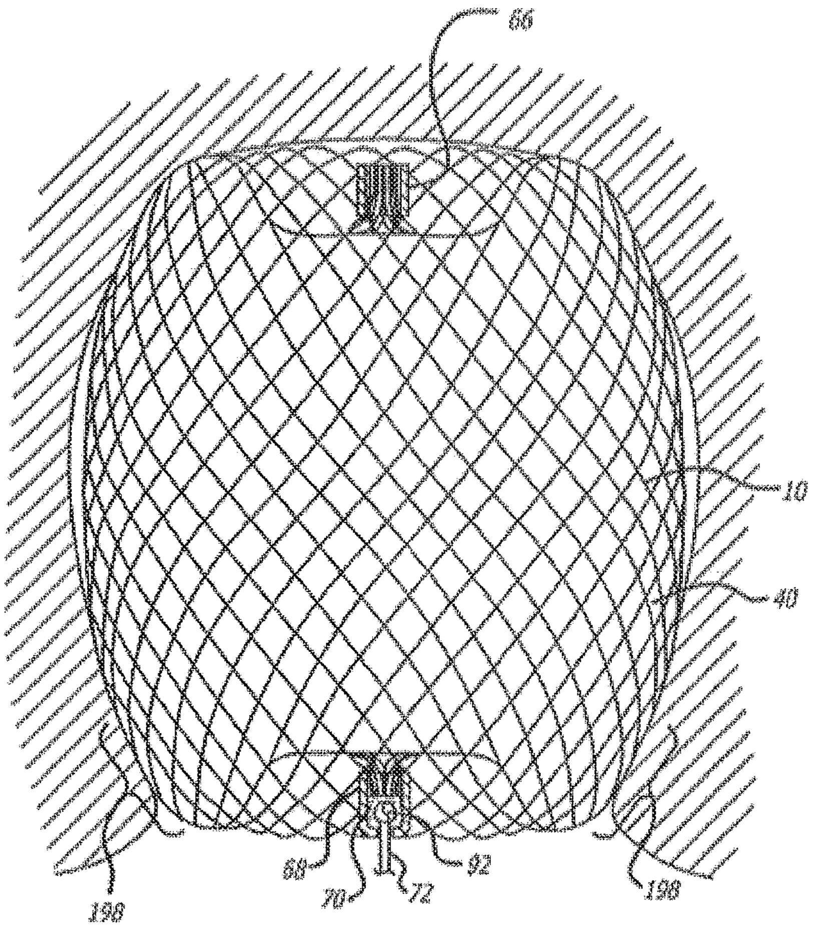
FIG. 29 shows an elevation view in section of a device for treatment of a patient's vasculature deployed within a vascular defect aneurysm.

Engagement of the permeable shell 40, 340, 440 with tissue of an inner surface of a vascular defect 160, when in an expanded relaxed state, may be achieved by the exertion of an outward radial force against tissue of the inside surface of the cavity of the patient's vascular defect 160, as shown for example in FIG. 29. A similar outward radial force may also be applied by a proximal end portion and permeable shell 40, 340, 440 of the device 10, 310, 410 so as to engage the permeable shell 40 with an inside surface or adjacent tissue of the vascular defect 160. Such forces may be exerted in some embodiments wherein the nominal outer transverse dimension or diameter of the permeable shell 40 in the relaxed unconstrained state is larger than the nominal inner transverse dimension of the vascular defect 160 within which the device 10, 310, 410 is being deployed, i.e., oversizing as discussed above. The elastic resiliency of the permeable shell 40 and filaments 14 thereof may be achieved by an appropriate selection of materials, such as superelastic alloys, including nickel titanium alloys, or any other suitable material for some embodiments. The conformability of a proximal portion of the permeable shell 40, 340, 440 of the device 10, 310, 410 may be such that it will readily ovalize to adapt to the shape and size of an aneurysm neck 190, as shown in FIGS. 20-22, thus providing a good seal and barrier to flow around the device. Thus, the device 10 may achieve a good seal, substantially preventing flow around the device without the need for fixation members that protrude into the parent vessel.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A device for treatment of a patient's cerebral aneurysm, comprising:

a first permeable shell including a first end, a second end, a radially constrained elongated state configured for delivery within a catheter lumen, an expanded state, and a plurality of filaments that are woven together to form a mesh, wherein each of the plurality of filaments has a first end and a second end, wherein each of the plurality of filaments starts at the first end of the first permeable shell, extends to the second end of the first permeable shell, and extends back to the first end of the first permeable shell to form an inverted portion, and wherein the first and second ends of each of the plurality of filaments are gathered in a hub at the first end of the first permeable shell; and a scaffolding structure wherein an expanded configuration, a plurality of scaffolding filaments positioned at a proximal region of the first permeable shell, wherein the scaffolding structure has an open proximal end and an open distal end, wherein, in the expanded state of the scaffolding structure, the open distal end comprises a scalloped shape, wherein the plurality of scaffolding filaments is different than the plurality of filaments of the first permeable shell, wherein the plurality of scaffolding filaments each comprise a straight portion extending from a proximal end to a distal scalloped end, wherein the inverted portion extends through the open distal end of the scaffolding structure.

2. The device of claim 1, wherein the plurality of scaffolding filaments are woven into the mesh of the first permeable shell.

3. The device of claim 1, wherein the scaffolding structure is coupled to the first permeable shell.

4. The device of claim 1, wherein the scaffolding structure is coupled to the first permeable shell using welding, adhesive, or mechanical ties.

5. The device of claim 1, wherein the first permeable shell comprises a cavity extending from the second end to the first end of the first permeable shell.

6. The device of claim 5, wherein the cavity is conical shaped.

7. The device of claim 5, wherein the cavity is cylindrical shaped.

8. The device of claim 1, wherein each of the plurality of scaffolding filaments has a diameter between about 0.001" and about 0.004".

9. The device of claim 1, wherein the scaffolding structure has a height, and wherein the height of the scaffolding structure is between about 10 and about 60% of a height of the first permeable shell.

10. The device of claim 1, wherein each of the plurality of scaffolding filaments has a diameter that is larger than a diameter of each of the plurality of elongate filaments of the first permeable shell.

11. The device of claim 1, wherein the first permeable shell comprises a distal opening communicating with the inverted portion.

12. The device of claim 11, wherein the inverted portion extends along a vertical axis of the first permeable shell.

13. The device of claim 1, wherein the plurality of filaments is a tubular braided structure.

14. The device of claim 1, wherein the plurality of filaments comprises filaments having 2 different diameters.

15. The device of claim 1, wherein the plurality of filaments comprises filaments having 3 different diameters.

16. The device of claim 1, wherein the plurality of filaments comprises DFT.

17. The device of claim 1, wherein the scaffolding structure is coupled to the proximal region of the first permeable shell.

18. The device of claim 1, wherein each of the plurality of filaments have a diameter between about 0.0003" and about 0.00125".

19. The device of claim 1, wherein the plurality of filaments comprises between about 4 to 48 wires.

20. The device of claim 1, wherein, in the expanded state of the scaffolding structure, at least a portion of the plurality of scaffolding filaments extend distally from the proximal end and curve back in a proximal direction to form a curved shape in a distal region, wherein the scalloped shape comprises a plurality of curved shapes formed from the at least a portion of the plurality of scaffolding filaments.

* * * * *